United States Patent
Lei

(10) Patent No.: US 9,574,989 B2
(45) Date of Patent: Feb. 21, 2017

(54) LENS-FREE IMAGING SYSTEM AND METHOD FOR DETECTING PARTICLES IN SAMPLE DEPOSITED ON IMAGE SENSOR

(71) Applicant: OmniVision Technologies, Inc., Santa Clara, CA (US)

(72) Inventor: Junzhao Lei, San Jose, CA (US)

(73) Assignee: OmniVision Technologies, Inc., Santa Clara, CA (US)

( * ) Notice: Subject to any disclaimer, the term of this patent is extended or adjusted under 35 U.S.C. 154(b) by 307 days.

(21) Appl. No.: 14/455,182

(22) Filed: Aug. 8, 2014

(65) Prior Publication Data

US 2016/0041094 A1 Feb. 11, 2016

(51) Int. Cl.
| | |
|---|---|
| G01N 21/00 | (2006.01) |
| G01N 15/14 | (2006.01) |
| G01N 21/64 | (2006.01) |
| G01N 15/00 | (2006.01) |
| G01N 15/10 | (2006.01) |

(52) U.S. Cl.
CPC ...... *G01N 15/1463* (2013.01); *G01N 15/1436* (2013.01); *G01N 21/6456* (2013.01); *G01N 2015/0065* (2013.01); *G01N 2015/1006* (2013.01); *G01N 2015/1465* (2013.01); *G01N 2015/1493* (2013.01); *G01N 2015/1497* (2013.01)

(58) Field of Classification Search
CPC ........... G01N 21/00; G01N 21/05; H04N 7/18
USPC ........................................ 250/216, 573, 576
See application file for complete search history.

(56) References Cited

U.S. PATENT DOCUMENTS

| | | | |
|---|---|---|---|
| 2007/0207061 A1* | 9/2007 | Yang | .................. G01N 21/6458 422/82.05 |
| 2010/0119172 A1 | 5/2010 | Yu et al. | |
| 2012/0098950 A1 | 4/2012 | Zheng et al. | |
| 2012/0114262 A1 | 5/2012 | Yu et al. | |
| 2012/0223217 A1* | 9/2012 | Zheng | ..................... B01L 3/508 250/215 |
| 2014/0193892 A1 | 7/2014 | Mohan et al. | |

FOREIGN PATENT DOCUMENTS

| | | | |
|---|---|---|---|
| CN | 103154662 A | 6/2013 | |
| TW | 201413232 A | 4/2014 | |

OTHER PUBLICATIONS

English translation of the First Office Action corresponding to Taiwanese Patent Application No. 104123446, received Aug. 24, 2016, 5 pages.

* cited by examiner

*Primary Examiner* — Kevin Pyo
(74) *Attorney, Agent, or Firm* — Lathrop & Gage LLP

(57) ABSTRACT

A lens-free imaging system for detecting particles in a sample deposited on image sensor includes a fluidic chamber for holding a sample and an image sensor for imaging the sample, wherein the image sensor has a light receiving surface and a plurality of photosensitive pixels disposed underneath the light receiving surface, and wherein the fluidic chamber formed at least in part by the light receiving surface. A method for detecting particles of interest in a sample deposited on an image sensor, through lens-free imaging using the image sensor, includes (ii) generating an image of the sample, deposited on a light receiving surface of the image sensor, by illuminating the sample, and (ii) detecting the particles of interest in the image.

25 Claims, 15 Drawing Sheets

LENS-FREE IMAGING SYSTEM AND METHOD FOR DETECTING PARTICLES IN SAMPLE DEPOSITED ON IMAGE SENSOR

BACKGROUND

A variety of medical diagnostic tests rely on identifying the presence and frequently the concentration of biological particles, such as different types of blood cells, bacteria and pathogens. Such tests include whole blood counting and concentration assessment of white blood cells for immunology-related diagnostics. Preferably, diagnostics systems quickly and inexpensively deliver accurate results without requiring highly trained technical staff. A flow cytometer is the standard diagnostics device for tests that rely on counting different types of blood cells. In a flow cytometer, a sample flows through a detection zone, typically one cell at a time, and cell properties are determined by an illumination and detection system. Based upon the measured properties, detected cells are grouped into categories to obtain the cell-type concentration of interest. Unfortunately, a flow cytometer is an expensive and complex instrument.

SUMMARY

In an embodiment, a lens-free imaging system for detecting particles in a sample deposited on image sensor includes a fluidic chamber for holding a sample and an image sensor for imaging the sample, wherein the image sensor has a light receiving surface and a plurality of photosensitive pixels disposed underneath the light receiving surface, and wherein the fluidic chamber formed at least in part by the light receiving surface.

In an embodiment, a method for detecting particles of interest in a sample deposited on an image sensor, through lens-free imaging using the image sensor, includes (ii) generating an image of the sample, deposited on a light receiving surface of the image sensor, by illuminating the sample, and (ii) detecting the particles of interest in the image.

DETAILED DESCRIPTION OF THE EMBODIMENTS

Figure 1:
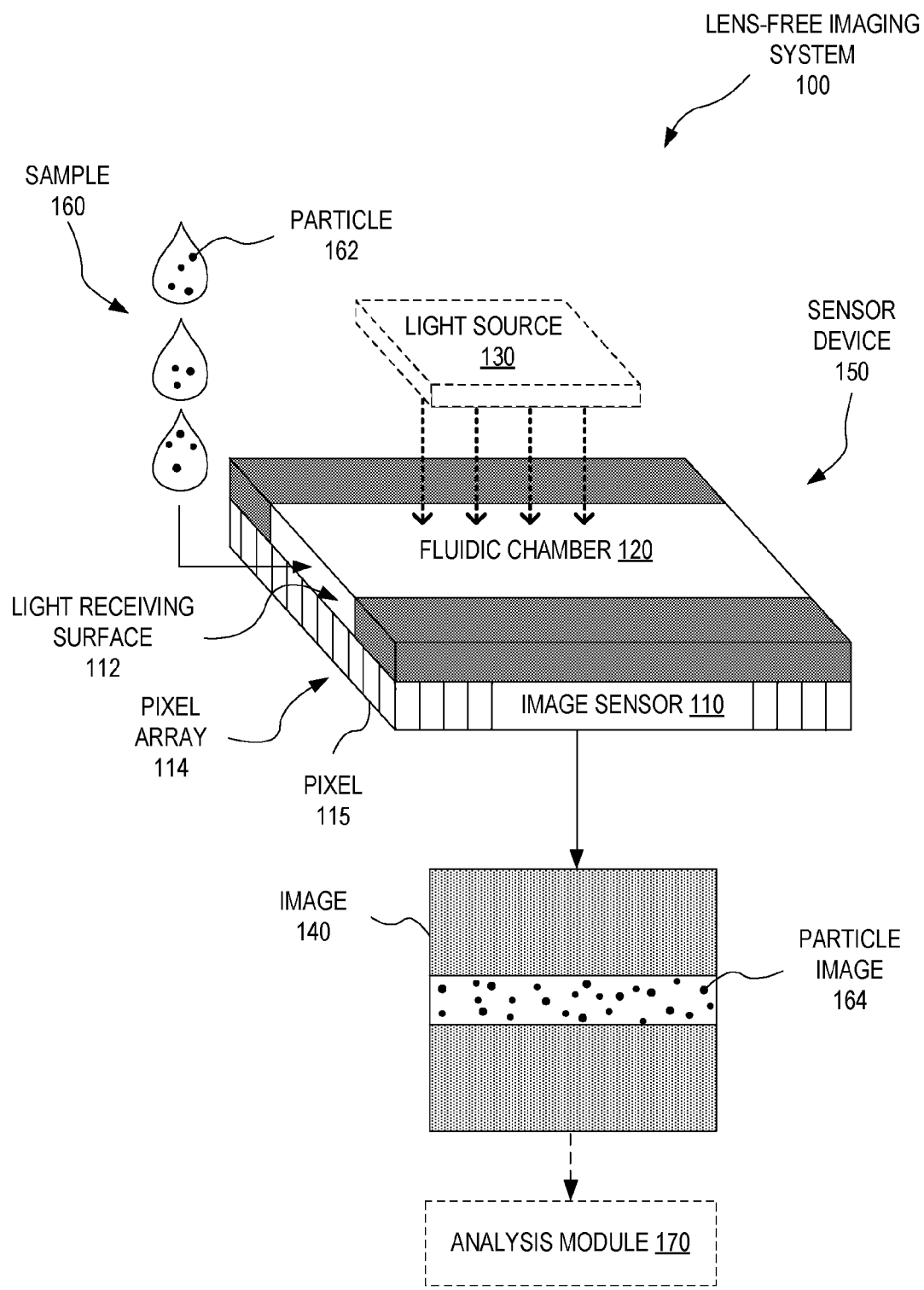
FIG. 1 illustrates one lens-free imaging system for detecting particles in a sample deposited on an image sensor, according to one embodiment.

FIG. 1 illustrates one exemplary lens-free imaging system 100 for detecting particles 162 in a sample 160 deposited on a sensor device 150. Sensor device 150 has an image sensor 110 and a fluidic chamber 120 disposed directly on a light receiving surface 112 of image sensor 110 that is in close proximity to photosensitive pixel elements 115 of image sensor 110. Lens-free imaging system 100 may include a light source 130 that illuminates fluidic chamber 120 and thus at least a portion of a sample 160 containing particles 162 therewithin.

Since fluidic chamber 120 is disposed directly on light receiving surface 112 and in close proximity to a photosensitive pixel array 114 (composed of photosensitive pixels 115) of image sensor 110, there is no need to include an imaging objective that images particles 162 of sample 160 onto photosensitive pixel array 114 of image sensor 110. Thus, lens-free imaging system 100 does not include an imaging objective between fluidic chamber 120 and photosensitive pixel array 114 and instead performs "lens-free imaging" of sample 160 when in fluidic chamber 120. In the present disclosure, "lens-free imaging" refers to imaging without use of an imaging objective, i.e., the image is formed on image sensor 110 without use of focusing (refractive or diffractive) elements, such as a lens or a pinhole aperture, to form the image. Lens-free imaging system 100 instead utilizes the close proximity between fluidic chamber 120 and photosensitive pixel array 114 to generate one or more images 140 of sample 160 in fluidic chamber 120 using image sensor 110. Particles 162 of sample 160 may be visible in image 140 as particle images 164. For clarity of illustration, only one particle 162, one particle image 164, and one pixel 115 are labeled in FIG. 1. Although FIG. 1 shows pixel array 114 as extending to the edges of image sensor 110, pixel array 114 may occupy only a portion of image sensor 110 without departing from the scope hereof. Likewise, pixel array 114 may be recessed from light receiving surface 112 into image sensor 110 without departing from the scope hereof.

Optionally, lens-free imaging system 100 includes an analysis module 170 that analyzes images 140 to obtain results, such as the number and/or concentration of particles of interest.

Sample 160 is, for example, a blood sample, a human blood sample, a nasal swab sample, a urine sample, or another biological sample. Particles 162 of interest in sample 160 may include one or more of blood cells, tissue cells, bacteria, and pathogens.

In an embodiment, image sensor 110 is a complementary metal oxide semiconductor (CMOS) image sensor. For example, image sensor 110 is a backside illuminated CMOS image sensor with improved light sensitivity, as compared to a frontside illuminated CMOS image sensor. Alternatively, image sensor 110 is a charge-coupled device (CCD) image sensor. Light source 130 is, for example, a light emitting diode (LED) or a plurality of LEDS that emit visible light. Light source 130 may include a focusing element that directs light towards fluidic chamber 120, for example to focus light onto fluidic chamber 120 or to provide collimated light to fluidic chamber 120. In another example, light source 130 includes a laser diode. Light source 130 may be integrated on sensor device 150, for example above fluidic chamber 120, without departing from the scope hereof.

Lens-free imaging system 100 provides simple and relatively inexpensive detection of particles such as a certain type of blood cell. Since lens-free imaging system 100 performs lens-free imaging of sample 160, the manufacture of lens-free imaging system 100 does not require the manufacture of an imaging objective nor alignment of an imaging objective with respect to image sensor 110 and/or light source 130; this simplifies manufacture of lens-free imaging system 100, and reduces the amount of material included in lens-free imaging system 100, and improves compactness. Hence, lens-free imaging system 100 may provide a more compact and cost-effective solution than competing lens-based imaging systems.

In certain embodiments, the imaged portion of fluidic chamber 120 has a known volume such that the concentration of a particular particle type may be deduced from the number of particles detected in images 140. In one embodiment, lens-free imaging system 100 is operated in a static mode, wherein sample 160 is first loaded into fluidic chamber 120 and then imaged by image sensor 110 while being stationary therein. In another embodiment, lens-free imaging system is operated in a flow mode, wherein sample 160 is imaged by image sensor 110 while flowing through fluidic chamber 120. The latter embodiment allows for imaging of a sample volume in excess of the volume of fluidic chamber 120. Optionally, the flow of sample 160 through fluidic chamber 120 is interrupted during imaging to generate a series of images 140, each representing a static image of a different portion of sample 160. This embodiment of lens-free imaging system 100 may include pumping sample 160 through fluidic chamber 120 using appropriate mechanics. Image 140 is, for example, a shadow image or a fluorescence image.

After completing imaging of sample 160, sample 160 may be cleaned out of fluidic chamber 120 to prepare sensor device 150 for imaging of another sample 160, such that sensor device 150 is reusable for imaging of multiple different samples 160.

Figure 2A:
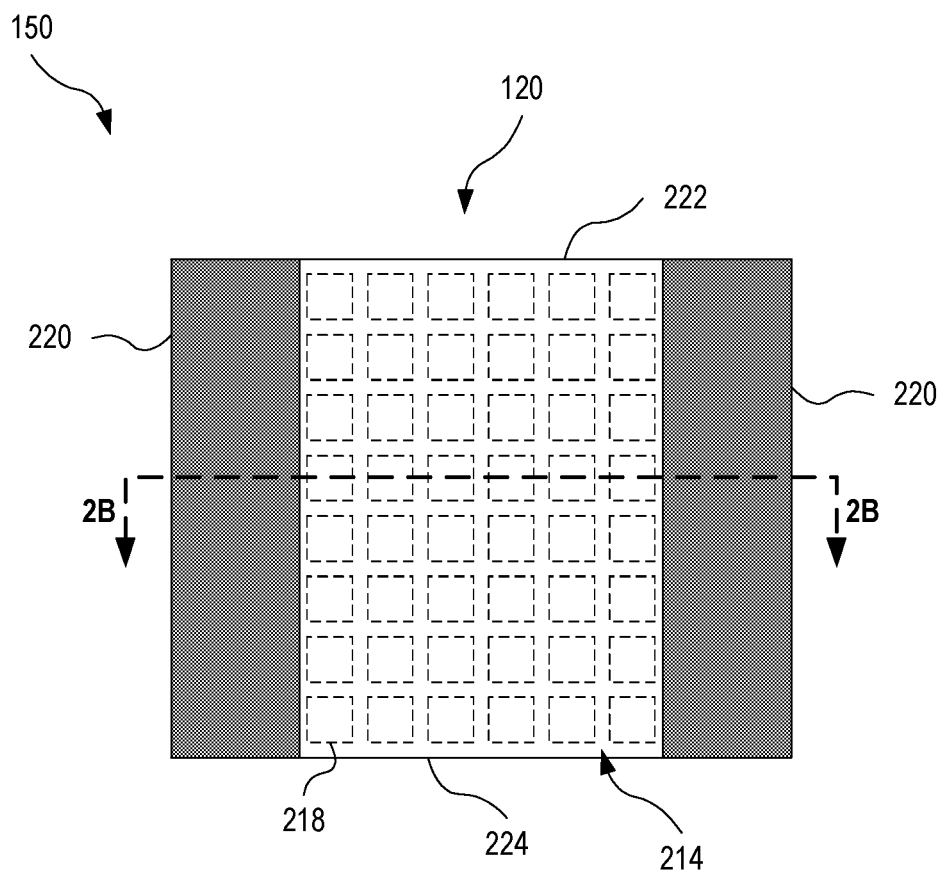
FIGS. 2A and 2B illustrate a sensor device including an image sensor for lens-free imaging of particles in a sample deposited on the image sensor, according to an embodiment.
Figure 2B:
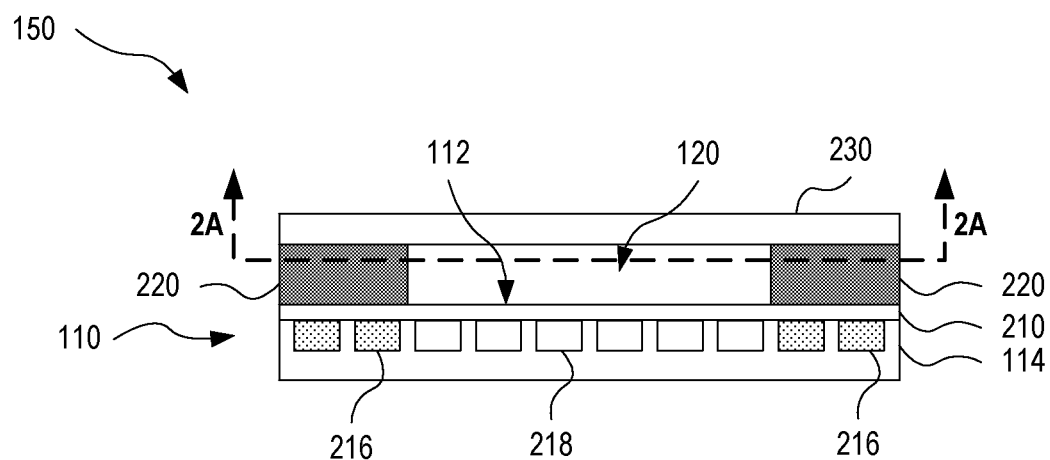

FIGS. 2A and 2B illustrate further exemplary details of sensor device 150 (FIG. 1). FIG. 2A shows sensor device 150 in cross sectional view, where the cross section is taken in the plane of image sensor 110. FIG. 2B shows sensor device 150 in cross sectional view, where the cross section is taken in a plane orthogonal to the plane of image sensor 110 along line 2B-2B of FIG. 2A.

Light receiving surface 112 is either the surface of pixel array 114 or, as illustrated in FIG. 2B, the top of a layer 210 disposed on pixel array 114. In an embodiment, the distance between light receiving surface 112 and pixel array 114 is significantly smaller than the size of particles 162 under interrogation using sensor device 150. For example, the distance between light receiving surface 112 and pixel array 114 is less than 10% of the diameter of such particles, or of other relevant physical dimensions such as length or width. In another embodiment, the shortest distance between a location in fluidic chamber 120 to pixel array 114 is much smaller than the size of particles 162. For example, the shortest distance is less than 10% of the diameter, or other relevant physical dimension such as length or width, of a particle of interest. The close proximity of either of these two embodiments facilitates lens-free imaging of sample 160 (FIG. 1), deposited in fluidic chamber 120, using image sensor 110.

Light receiving surface 112, walls 220 and a cover 230 form fluidic chamber 120 in the embodiment of FIGS. 2A and 2B. Walls 220 are for example opaque and cover 230 is at least partially transmissive to light. Hence, at least a portion of light generated by a light source 130 may pass through cover 230 to illuminate sample 160 in fluidic chamber 120. Walls 220 may be formed from a flexible laminate adhered to light receiving surface 112 and cover 230, such as a double-sided adhesive. Alternatively, walls 220 may be formed from one or more rigid spacers bonded to light receiving surface 112 and cover 230. Walls 220 are also disposed over a portion of pixel array 114, e.g., over pixels 216 of array 114; pixels 218 on the other hand are located underneath fluidic chamber 120 to image sample 160 therein. Pixels 216 and 218 are embodiments of pixels 115 (FIG. 1). For clarity of illustration, only one pixel 218 is labeled in each of FIGS. 2A and 2B. Pixels that are not located underneath fluidic chamber 120, i.e., pixels 216, may be dark pixels. Dark pixels are pixels that do not receive light and therefore may be utilized to evaluate electronic noise, for example associated with pixel readout. For clarity of illustration, not all pixels 216 are labeled in FIG. 2B.

Pixel array 114 may contain more pixels than illustrated in FIGS. 2A and 2B without departing from the scope hereof. Likewise, a smaller or larger portion of pixel array 114 may be located underneath fluidic chamber 120, and fluidic chamber 120 may furthermore have a different shape than illustrated in FIG. 2A, again without departing from the scope hereof. For example, fluidic chamber 120 may occupy a rectangular portion of light receiving surface 112 having a large aspect ratio. In one embodiment, each pixel 218 of pixel array 114 includes a microlens that focuses light incident on the pixel onto a photodiode thereof. Since each of such microlenses only operates on an individual pixel 218, they do not contribute to image formation on pixel array 114. In another embodiment, pixels of pixel array 114 are lens-free, simplifying manufacture of sensor device 150. Likewise, a color filter, such as a Bayer filter that enables color image capture by image sensor 110 is not necessarily required. Hence, in certain embodiments, image sensor 110 is a monochromatic image sensor.

As illustrated in FIG. 2A, fluidic chamber 120 includes two fluidic ports 222 and 224. Although FIG. 2A shows fluidic ports 222 and 224 as being formed by the gap between light receiving surface 112 and cover 230 at the edge of sensor device 150, one or both of fluidic ports 222 and 224 may be formed as a hole in cover 230 without departing from the scope hereof.

In an embodiment, light receiving surface 112, and, optionally, portions of walls 220 and cover 230 forming fluidic channel 120, are corrosion resistant such that fluids in fluidic chamber 120 do not cause corrosion damage to light receiving surface 112, and other surfaces in contact with sample 160. Light receiving surface 112, and portions of walls 220 and cover 230 forming fluidic channel 120 may therefore be biocompatible such that a sample in fluidic chamber 120 is not affected by the materials of interior surface of fluidic chamber 120.

Figure 3:
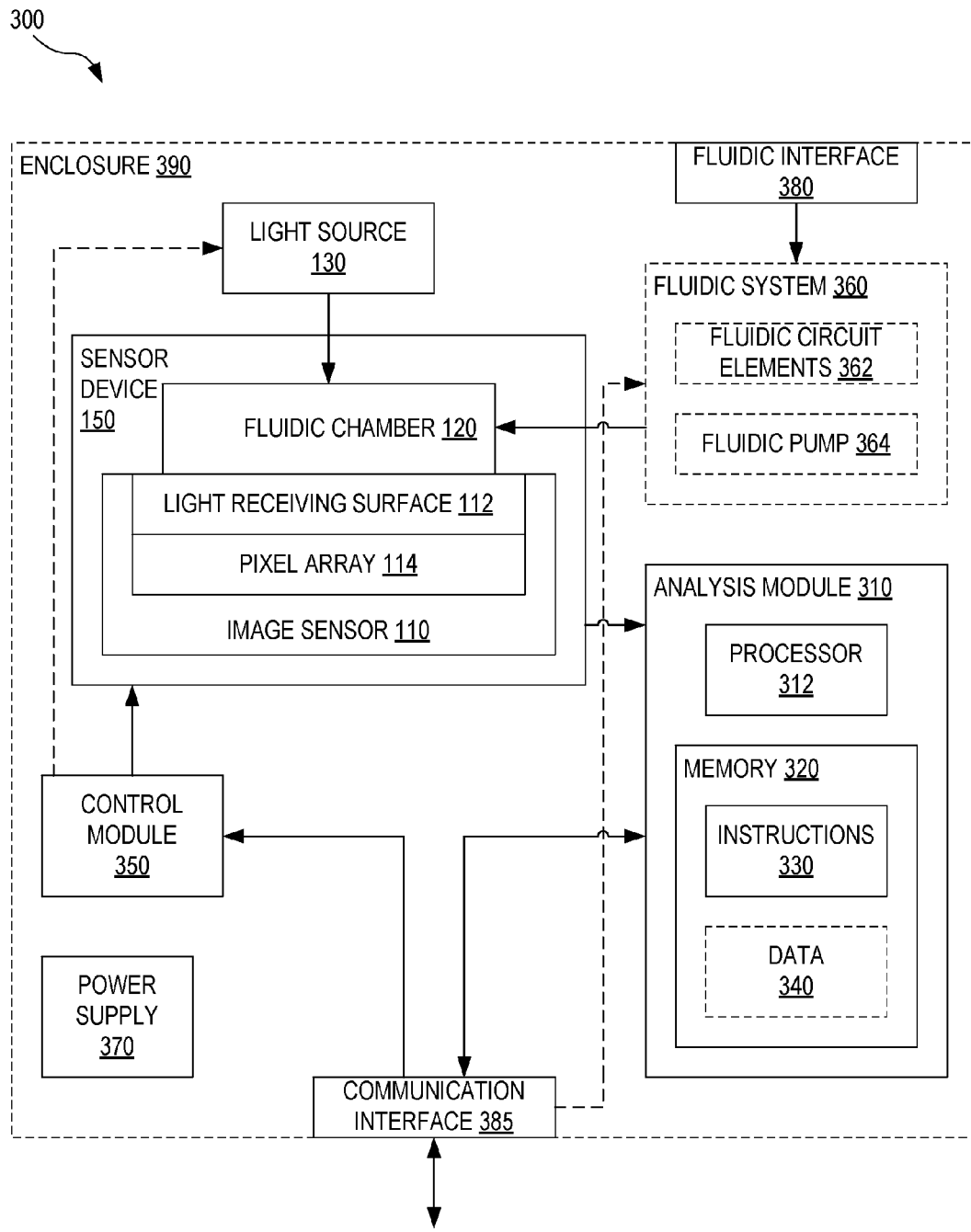
FIG. 3 illustrates one lens-free imaging system for detecting particles in a sample deposited on an image sensor, which includes the sensor device of FIG. 2, according to an embodiment.

FIG. 3 illustrates one exemplary lens-free imaging system 300 for detection of particles in a sample deposited on the image sensor used to image the sample. Lens-free imaging system 300 is an embodiment of lens-free imaging system 100 (FIG. 1). At least a portion of lens-free imaging system 300 is integrated on image sensor 110 of FIG. 1. Lens-free imaging system 300 includes sensor device 150 (FIGS. 1, 2A, and 2B), light source 130 (FIG. 1), and a control module 350. Control module 350 controls at least portions of the functionality of sensor device 150 and, optionally, operation of light source 130. Light source 130 illuminates fluidic chamber 120, which, as shown in FIGS. 2A and 2B, is in direct contact with light receiving surface 112 (FIG. 2B). At least a portion of pixel array 114 (FIGS. 2A and 2B) captures an image of fluidic chamber 120 through light receiving surface 112.

Lens-free imaging system 300 is shown with an analysis module 310 that analyzes images captured by image sensor 110. Analysis module 310 is an embodiment of analysis module 170 (FIG. 1) that includes a processor 312 and memory 320. Memory 320 includes machine-readable instructions 330 encoded in a non-volatile portion of memory 320. Optionally, memory 320 further includes a data storage 340 for storing images captured by image sensor 110 and/or data extracted therefrom.

In an embodiment, lens-free imaging system 300 includes an enclosure 390. Although not illustrated in FIG. 3, lens-free imaging system 300 may be configured as a readout instrument that receives sensor device 150 to image a sample therewithin.

Lens-free imaging system 300 includes a communication interface 385 for communicating with an operator or an external system such as an external computer. Communication interface 385 receives commands from the operator or the external system and communicates these instructions to control module 350 and/or analysis module 310. Communication interface 385 also serves to communicate data, such as images of fluidic chamber 120 and/or data extracted therefrom, from analysis module 310 to an operator or an external system. Although not illustrated in FIG. 3, communication interface 385 may receive images, captured by image sensor 110, directly from image sensor 110 and without departing from the scope hereof.

Furthermore, lens-free imaging system 300 includes a power supply 370 that supplies power to one or more of image sensor 110, light source 130, analysis module 310, and communication interface 385.

In one embodiment, control module 350, analysis module 310, communication interface 385, power supply 370, and, optionally, light source 130, are integrated on a common integrated circuit board. In another embodiment, one or more of power supply 370, control module 350, and analysis module 310 are located externally to lens-free imaging system 300, and communicate with particle identification system 300 through communication interface 385.

Sensor device 150 may be incorporated in lens-free imaging systems different from lens-free imaging system 300, or exist as a standalone device, without departing from the scope hereof.

Figure 4:
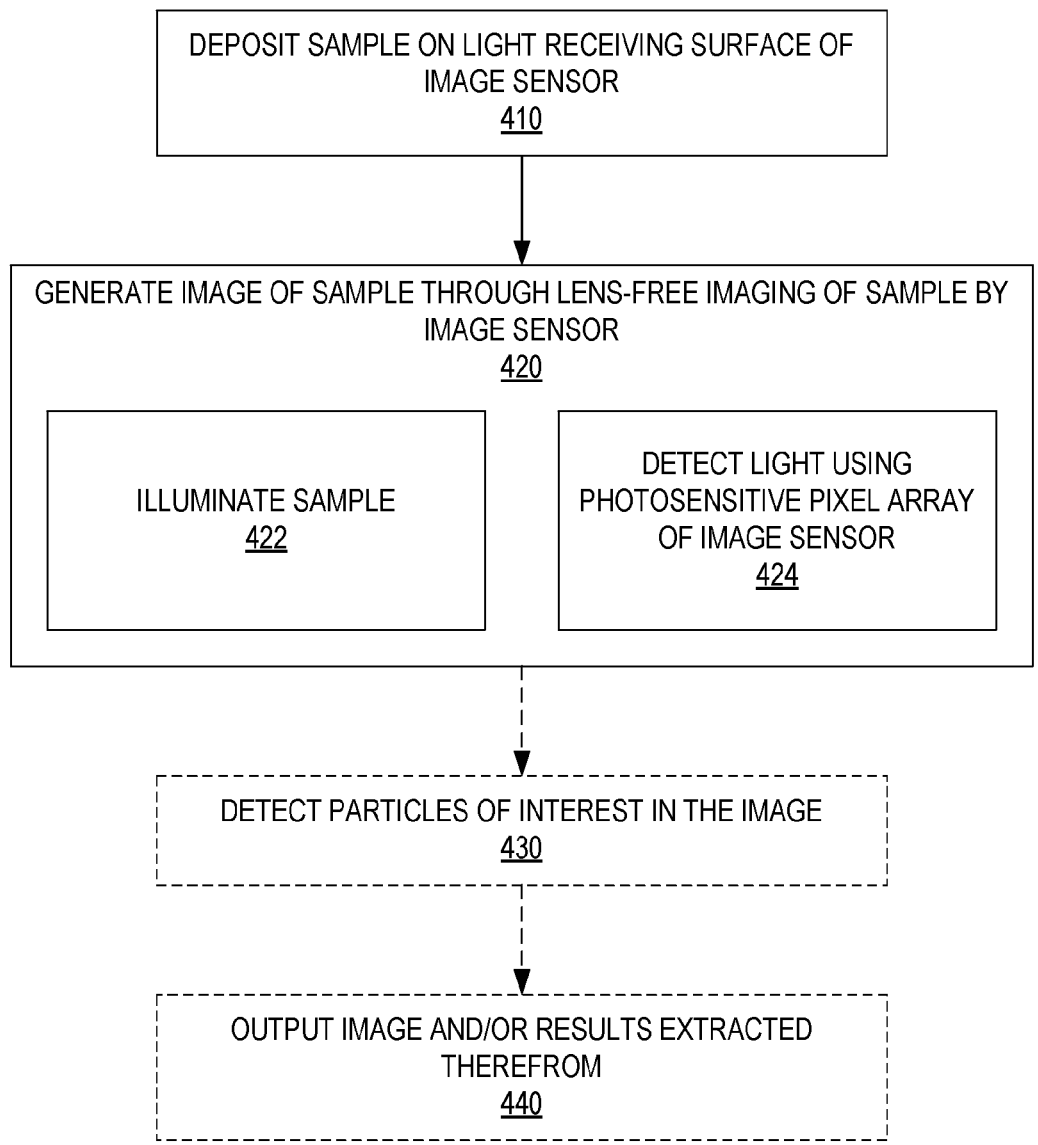
FIG. 4 illustrates one lens-free imaging method for detecting particles in a sample deposited on an image sensor, according to an embodiment.

FIG. 4 illustrates one exemplary method 400 for detecting particles in a sample deposited on an image sensor, using lens-free imaging by the image sensor of the sample. Method 400 utilizes lens-free imaging of a sample disposed in a fluidic chamber integrated on the light receiving surface of the image sensor used for imaging the sample. Method 400 is performed, for example, by lens-free imaging systems 100 or 300 of FIGS. 1 and 3, respectively.

In a step 410, the sample is deposited on the light receiving surface of the image sensor. For example, sample 160 (FIG. 1) is deposited in fluidic chamber 120 (FIGS. 1, 2A, 2B, and 3) on light receiving surface 112 (FIGS. 2A, 2B, and 3) of image sensor 110 (FIGS. 1, 2A, 2B, and 3).

In a step 420, the image sensor, onto which the sample is deposited in step 410, performs lens-free imaging of the sample to produce an image thereof. For example, image sensor 110 generates an image of sample 160 deposited on light receiving surface 112 in step 410. Optionally, the execution of step 420 is controlled by control module 350 (FIG. 3), for example according to instructions received through communication interface 385 (FIG. 3). Alternatively, image sensor 110 is free-running and captures images at regular intervals when powered on. In certain embodiments, step 420 is repeated one or more times to generate a plurality of images of the sample.

Step 420 includes steps 422 and 424. In step 422, the sample is illuminated. For example, light source 130 (FIGS. 1 and 3) illuminates fluidic chamber 120 to illuminate sample 160 deposited therein. In step 424, the image sensor uses a photosensitive pixel array to detect light. For example, image sensor 110 uses pixel array 114 (FIGS. 1, 2A, 2B, and 3) to detect light incident on light receiving surface 112. Since fluidic chamber 120 is in direct contact with light receiving surface 112 of image sensor 110, a sample deposited in fluidic chamber 120 is in close proximity to pixel array 114. This facilitates lens-free imaging of the sample deposited in fluidic chamber 120.

In an optional step 430, particles of interest are detected in the image, or images, generated in step 420. For example, processor 312 (FIG. 3) of analysis module 310 (FIG. 3) executes instructions 330 (FIG. 3) to detect particles of interest in an image received from image sensor 110. Step 430 may further include processing detected particles of interest to produce other results, such as the number of concentration of one or more particles of interest or properties of one or more particles of interest.

In an optional step 440, images generated in step 420 and/or results extracted therefrom in optional step 430 are outputted. In one example, image sensor 110 outputs images generated by image sensor 110 to communication interfaced 385. In another example, analysis module 310 outputs images generated by image sensor 110 and/or results extracted therefrom in step 430 to communication interface 385.

Figure 5:
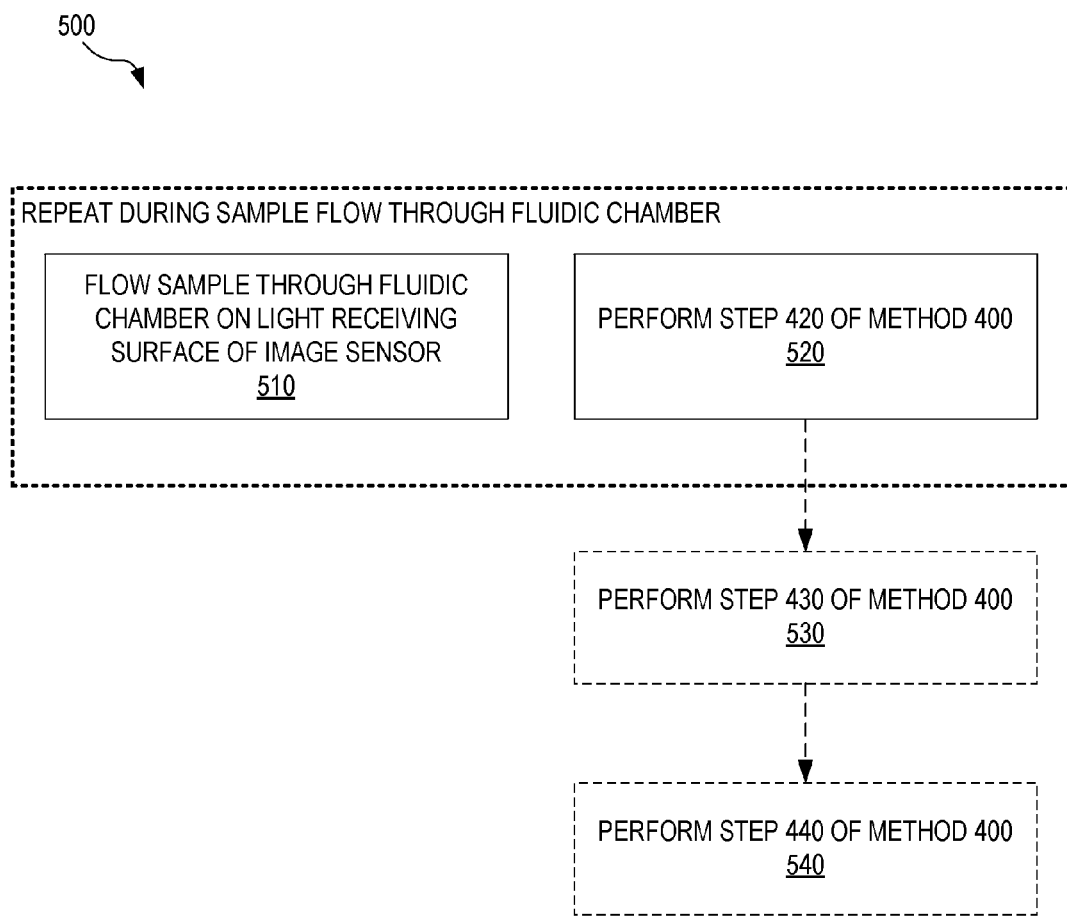
FIG. 5 illustrates one lens-free imaging method for detecting particles in a sample deposited on an image sensor, wherein the sample is flowing across the image sensor used to image the sample, according to an embodiment.

FIG. 5 illustrates one exemplary method 500 for detecting particles, utilizing lens-free imaging of a sample flowing through a fluidic chamber integrated on the light receiving surface of the image sensor used for imaging the sample.

Method 500 is performed, for example, by lens-free imaging systems 100 or 300 of FIGS. 1 and 3, respectively.

In a step 510, a sample is flowed through a fluidic chamber formed on the light receiving surface of an image sensor. For example, sample 160 (FIG. 1) is flowed through fluidic chamber 120 using methods know in the art. In a step 520, method 500 performs step 420 of method 400 (FIG. 4). Steps 510 and 520 are performed repeatedly to generate multiple images of a sample.

Optionally, method 500 includes one or both of steps 530 and 540 of performing steps 430 and 440, respectively, of method 400. Although illustrated in FIG. 5 as being performed subsequent to all repetitions of steps 510 and 520, steps 530 and 540 may be performed during repetitions of steps 510 and 520. For example, particle detection in step 530 may take place as soon as an image is generated in step 520.

Figure 6:
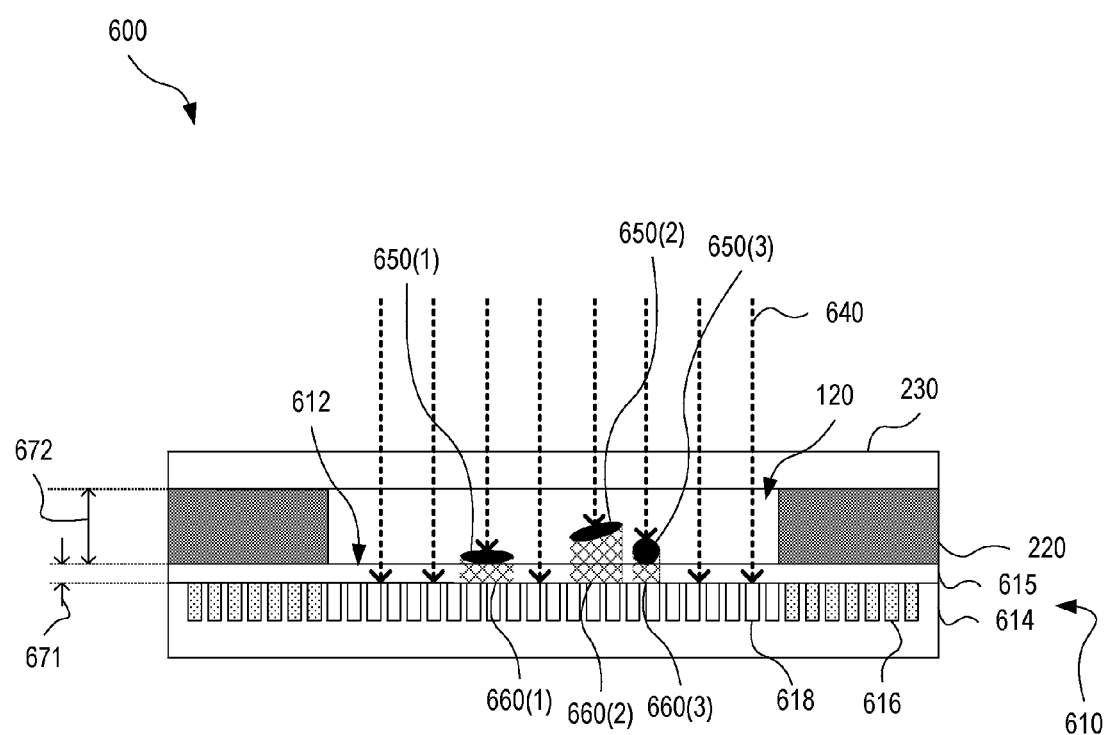
FIG. 6 illustrates a sensor device for lens-free shadow imaging of particles in a sample deposited on the image sensor used to image the sample, according to an embodiment.

FIG. 6 illustrates one exemplary sensor device 600 for performing lens-free imaging of a sample, such as sample 160 of FIG. 1, to generate a shadow image of the sample. Sensor device 600 is an embodiment of sensor device 150 (FIGS. 1, 2A, and 2B) tailored for shadow imaging a sample. Sensor device 600 includes an image sensor 610 and fluidic chamber 120 (FIGS. 1, 2A, and 2B) disposed thereupon. Image sensor 610 is an embodiment of image sensor 110 (FIGS. 1, 2A, and 2B). FIG. 6 depicts sensor device 600 in the same cross-sectional view as used in FIG. 2B for sensor device 150.

Image sensor 610 includes a light receiving surface 612 and a photosensitive pixel array 614. Light receiving surface 612 is, for example, the surface of pixel array 614 or, as illustrated in FIG. 6, provided by a layer 615 disposed on pixel array 614. Light receiving surface 612, pixel array 614, and layer 615 are embodiments of light receiving surface 112, pixel array 114, and layer 210, respectively, of FIGS. 2A and 2B. In an example, layer 615 is or includes an anti-reflective coating.

Fluidic chamber 120 is formed by light receiving surface 612 together with walls 220 (FIG. 2B) and cover 230 (FIG. 2B), similar to the case of sensor device 150 as discussed in connection with FIGS. 2A and 2B. Pixel array 614 includes pixels 618, located underneath fluidic chamber 120 for imaging of a sample therein, and pixels 616 located underneath walls 220. Pixels 616 may be dark pixels. Pixels 618 and 616 are embodiments of pixels 218 and 216, respectively, of FIG. 2B. For clarity of illustration, not all pixels 618 and 616 are labeled in FIG. 6.

Image sensor 610 is configured to capture a shadow image of a sample in fluidic chamber 120. The shadow image is formed by exposing fluidic chamber 120 to illumination 640, for example generated by light source 130 (FIG. 1). In the exemplary scenario illustrated in FIG. 6, illumination 640 is at least partially blocked by particles 650(1), 650(2), and 650(3) to form corresponding shadows 660(1), 660(2), and 660(3) on light receiving surface 612. Hence, particles 650(1), 650(2), and 650(3) are identifiable as shadows 660(1), 660(2), and 660(3), respectively, in a shadow image captured by image sensor 610 using pixel array 614. Illumination 640 may be substantially collimated, as illustrated in FIG. 6, or deviate from being collimated, without departing from the scope hereof. In an embodiment, sensor device 600 is configured to receive illumination 640 having wavelength in the visible spectrum, for example in the range from 400 nanometers to 600 nanometers.

In certain embodiments, sensor device 600 is configured to detect geometrical properties, such as size and/or shape, of particles in fluidic chamber 120 through determination of the size and shape of shadows associated with the particles. The accuracy, with which geometrical properties of particles of interest may be determined from images generated by sensor device 610, is affected by several properties of sensor device 600, including (a) the resolution of pixel array 614, (b) the wavelength of illumination 640, (c) the distance 671 from pixel array 614 to light receiving surface 612, and in some cases (d) the height 672 of fluidic chamber 120. These factors further determine the ability to properly identify and separate two or more particles located closely together. Properly identification and separation of such particles facilitates particle identification at high particle concentrations. In the following description, these factors are discussed in the context of determining geometrical properties of single particles. However, the discussion applies also to the determination of geometrical properties of clumped particles, for the purposes of identifying individual particles in a clump of particles.

In an embodiment, the size of pixels 618 is significantly smaller than the geometrical properties of interest for particles in fluidic chamber 120. For example, pixels 618 are sufficiently small that an image captured by image sensor 610 shows that shadow 660(3) is smaller than shadows 660(1) and 660(2). In this case, the image may hold the information required to determine that the cross-sectional area of particle 650(3), where the cross section is taken in a plane parallel with light receiving surface 612, is smaller than those of particles 650(1) and 650(2). In one exemplary use scenario, sensor device 600 is used to identify one or more types of human blood cells. Red blood cells generally have diameter of 6-8 microns, while white blood cells have diameters in the range from 8 to 18 microns. Accordingly, distinction between red blood cells and white blood cells may require submicron resolution, or at least resolution on the order of a micron. Hence, in an embodiment, pixels 618 have size on the order of one micron.

In an embodiment, the wavelength of illumination 640 and the distance from pixel array 614 to particles of interest in fluidic chamber 120 are matched to the size of the particles of interest to minimize or reduce diffraction effects in the image captured by image sensor 610. Diffraction occurs when illumination 640 interacts with particles in fluidic chamber 120. The degree to which a shadow formed by a particle on pixel array 614 exhibits diffraction effects is determined by the Fresnel number $F=a^2/\lambda d$, where $a$ is the characteristic size of the particle, such as the radius of the particle, $\lambda$ is the wavelength of illumination 640, and $d$ is the distance from the particle to pixel array 614. Fresnel numbers much smaller than one are representative of far-field diffraction, i.e., the observation screen is far from the particle relative to the size of the particle, and may be described in the approximation known as Fraunhofer diffraction. Fresnel numbers near one and greater than one are associated with near-field diffraction, where the observation no longer can be considered as being far away from the particle on the scale of the particle size. Near-field diffraction is described by Fresnel diffraction. Accurate or even approximate imaging of the outline of a particle requires that the image is formed in the near field with a Fresnel number greater than one. Therefore, accurate or even approximate imaging of the outline of a particle in fluidic chamber 120 requires that the distance from pixel array 614 to the particle is less than the characteristic size of the particle.

Figure 7:
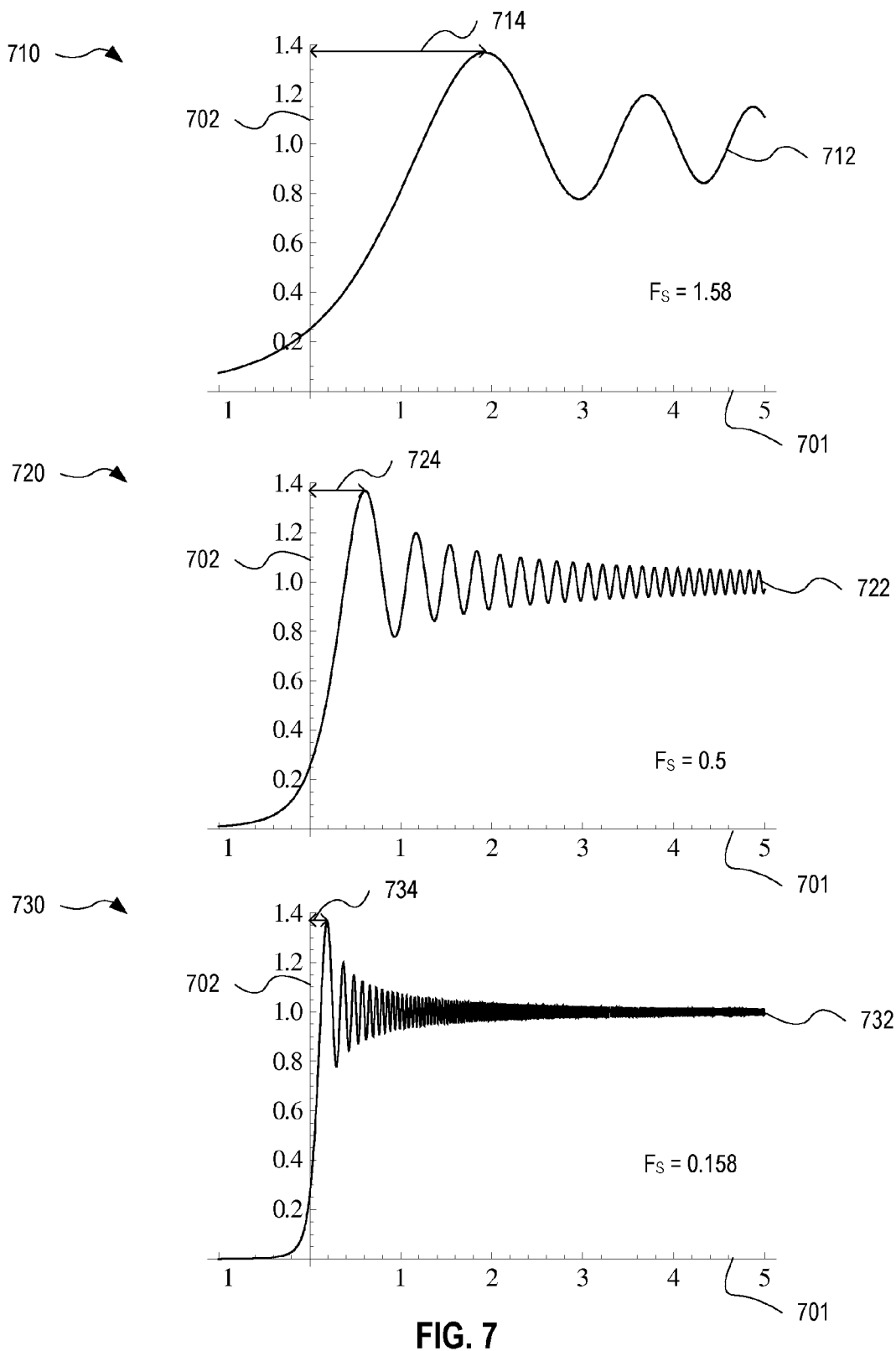
FIG. 7 illustrates diffraction effects for a plane wave of light incident on a straight edge obstacle.

FIG. 7 illustrates the effect of diffraction for a plane wave of light incident on a straight edge obstacle, where the area one side of the edge, extending away from the edge in a plane orthogonal to the propagation direction of incident light, is opaque, while the area on the other side of the edge is transparent. For a straight edge, the intensity I(x) of light observed on an observation screen positioned behind the edge may be expressed as $$I(x) = \frac{1}{2}\left\{\left[\frac{1}{2} - C\left(\sqrt{\frac{2}{\lambda d}} \cdot (-x)\right)\right]^2 + \left[\frac{1}{2} - S\left(\sqrt{\frac{2}{\lambda d}} \cdot (-x)\right)\right]^2\right\},$$

where C(x) and S(x) are the Fresnel integrals and x is the distance from the edge to an observation point in a direction orthogonal to the edge and orthogonal to the propagation direction of the incident light. The edge is located at x=0.

Plots 710, 720, and 730 show I(x) for three different Fresnel scales, where the Fresnel scale is given by $F_S=\sqrt{\lambda d/2}$. (Since the straight edge is infinite, there is no characteristic size scale, and therefore the Fresnel number does not apply to the straight edge example.) Each of plots 710, 720, and 730 shows the intensity profile I(x) plotted in arbitrary intensity units 702 as a function of x in units of micron. Negative values of x correspond to the opaque portion of the obstacle, while positive values of x correspond to the unobscured portion of space. Plot 710 shows the intensity profile I(x), labeled 712, for $F_S=1.58$. This example is representative of, for example, illumination 640 with a wavelength of 500 nanometers (nm) incident on a straight edge obstacle, in fluidic chamber 120, located a distance of 10 microns away from pixel array 114. The point of maximum intensity is shifted from the position of the edge by approximately 2 microns (indicated by arrow 714). Plot 720 shows the intensity profile I(x), labeled 722, for $F_S=0.5$. In this case, the point of maximum intensity is shifted from the edge by approximately 0.6 micron (indicated by arrow 724. This plot is representative of, for example, illumination 640 with a wavelength of 500 nanometers (nm) incident on a straight edge obstacle, in fluidic chamber 120, located a distance of one micron away from pixel array 114. Plot 730 shows the intensity profile I(x), labeled 732, for $F_S=0.158$. In this case, the point of maximum intensity is shifted from the edge by approximately 0.2 micron (indicated by arrow 724. This plot is representative of, for example, illumination 640 with a wavelength of 500 nanometers (nm) incident on a straight edge obstacle, in fluidic chamber 120, located a distance of 0.1 micron away from pixel array 114. In general, the shift of the point of maximum intensity away from the position of the edge may be considered a measure of the blur caused by diffraction.

Jennings et al. have shown (The Astronomical Journal, 118:3061-3067, 1999) that diffraction on relatively large, round obstacles may be treated in the straight edge approximation with only negligible deviation from the exact solution. Hence, at least the results of plots 720 and 730 are accurate representations of the shifts experienced for round particles, where the term round may refer to particles that are circular, elliptical, oblong, or a combination thereof. Some non-negligible deviation from the exact solution may exist in connection with plot 710. However, plot 710 applies to the present discussion in at least a qualitative fashion. At a Fresnel scale of 1.58, as depicted in plot 710, the shadow image of an obstacle will show a significantly blurred outline. The point of maximum intensity is shifted by about 2 microns, and the intensity profile is further associated with long-scale intensity oscillations extending many micron away from the actual location of the obstacle. For particles of interest with radius in the range between 3 and 10 microns, which is the typical range for human blood cells, the diffraction effects illustrated in plot 710 are significant. On the other hand, the shift 734 and the associated blur of the outline in the case of plot 730 are negligible and allows for accurate determination of the size of human blood cells. The shift 724 associated with plot 720 may also be sufficiently small to allow determination of size of human blood cells.

Figure 8:
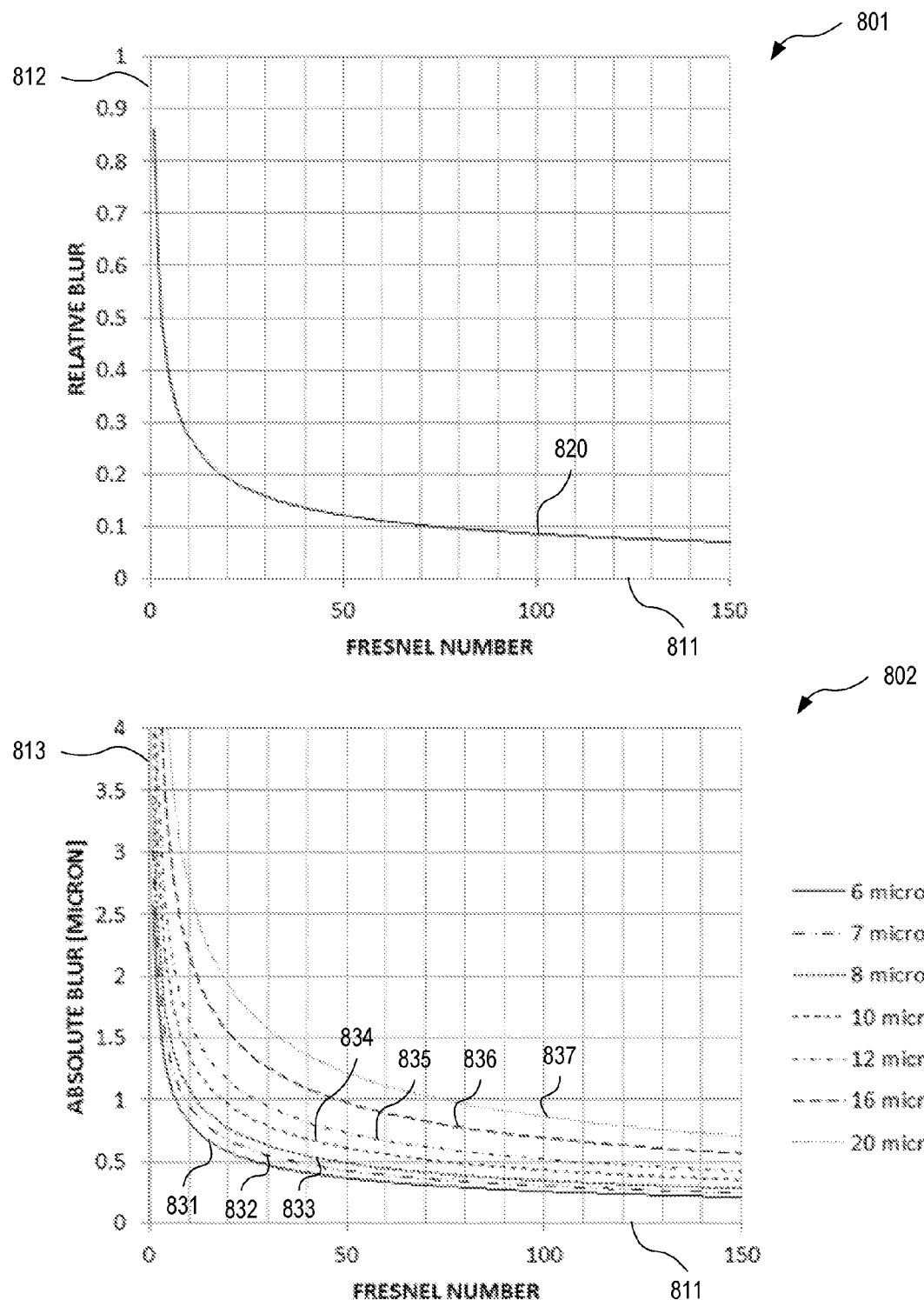
FIG. 8 illustrates a relationship between Fresnel number and diffraction-induced blur of a shadow in a shadow image, according to an embodiment.

FIG. 8 shows the relationship between Fresnel number and the shift of the point of maximum intensity, away from the actual location of a particle, for several different exemplary configurations of sensor device 600. In the straight edge approximation, the point of maximum intensity of light associated with a shadow, on pixel array 614 and of a particle in fluidic chamber 120, is shifted from the edge of the particle by $\Delta x=1.22F_S=1.22a\sqrt{1/2F}$. Thus, the shift $\Delta x$ may be expressed as a function of the characteristic size of the particle and the Fresnel number. The relative shift is defined as $\Delta x/a$ and may be expressed as $\Delta x/a=1.22\sqrt{1/2F}$. Accordingly, the relative shift may be expressed as a function of the Fresnel number alone.

Plot 801 shows the relative shift $\Delta x/a$, labeled 820, plotted as relative shift 812 versus Fresnel number 811. Plot 801 shows that a Fresnel number of approximately 75 or greater is required to obtain a relative shift of less than 10%. Plot 802 shows the absolute shift $\Delta x$, plotted as absolute shift in micron 813 versus Fresnel number 811, for several different particle diameters. Traces 831, 832, 833, 834, 835, 836, and 837 shows the absolute shift for particle diameters of 6 micron, 7 micron, 8 micron, 10 micron, 12 micron, 16 micron, and 20 micron, respectively.

As discussed above, distinction between red blood cells and white blood cells may require submicron resolution, or at least resolution on order of a micron. Likewise, near-micron or submicron resolution may be required to distinguish between different types of white blood cells. Therefore, in an embodiment, sensor device 600 is configured to cooperate with illumination 640 to result in a Fresnel number that is greater than 75, such that the relative shift is less than 10%, or less than one micron for a particle diameter of 10 microns. A relative shift of 10% or less amounts to submicron resolution for red blood cells and the smaller white blood cells. For example, the distance 671 from light receiving surface 612 to pixel array 614 is less than 0.67 micron, such that a particle of 10 micron diameter, located on light receiving surface 612 and illuminated with illumination 640 having wavelength 500 nm, is associated with a Fresnel number of at least 75. In another embodiment, distance 671 is less than 0.33 micron, such that a particle of 7 micron diameter, located on light receiving surface 612 and illuminated with illumination 640 having wavelength 500 nm, is associated with a Fresnel number of at least 75. In yet another embodiment, distance 671 is less than 0.33 micron, such that a particle of 7 micron diameter, such as a red blood cell located on light receiving surface 612 and illuminated with 500 nm light, is associated with a Fresnel number of 75. In a further embodiment, distance 671 is sufficiently small that the Fresnel number associated with illumination 640 and a particle of interest, located on light receiving surface 612, results in $\Delta x$ being less than the size of one pixel 618; wherein the size of a pixel is defined as the largest dimension of pixel 618 in a plane parallel to light receiving surface 612.

For imaging of particles that are dispersed throughout the sample away from light receiving surface 612, diffraction effects are minimized when the height 672 of fluidic chamber 120 is small. Therefore, in certain embodiments of sensor device 600, height 672 is the minimal height that allows for depositing the particles of interest in fluidic chamber 120. For example, for interrogation of human blood samples, height 672 is near or less than 20 microns.

Figure 9:
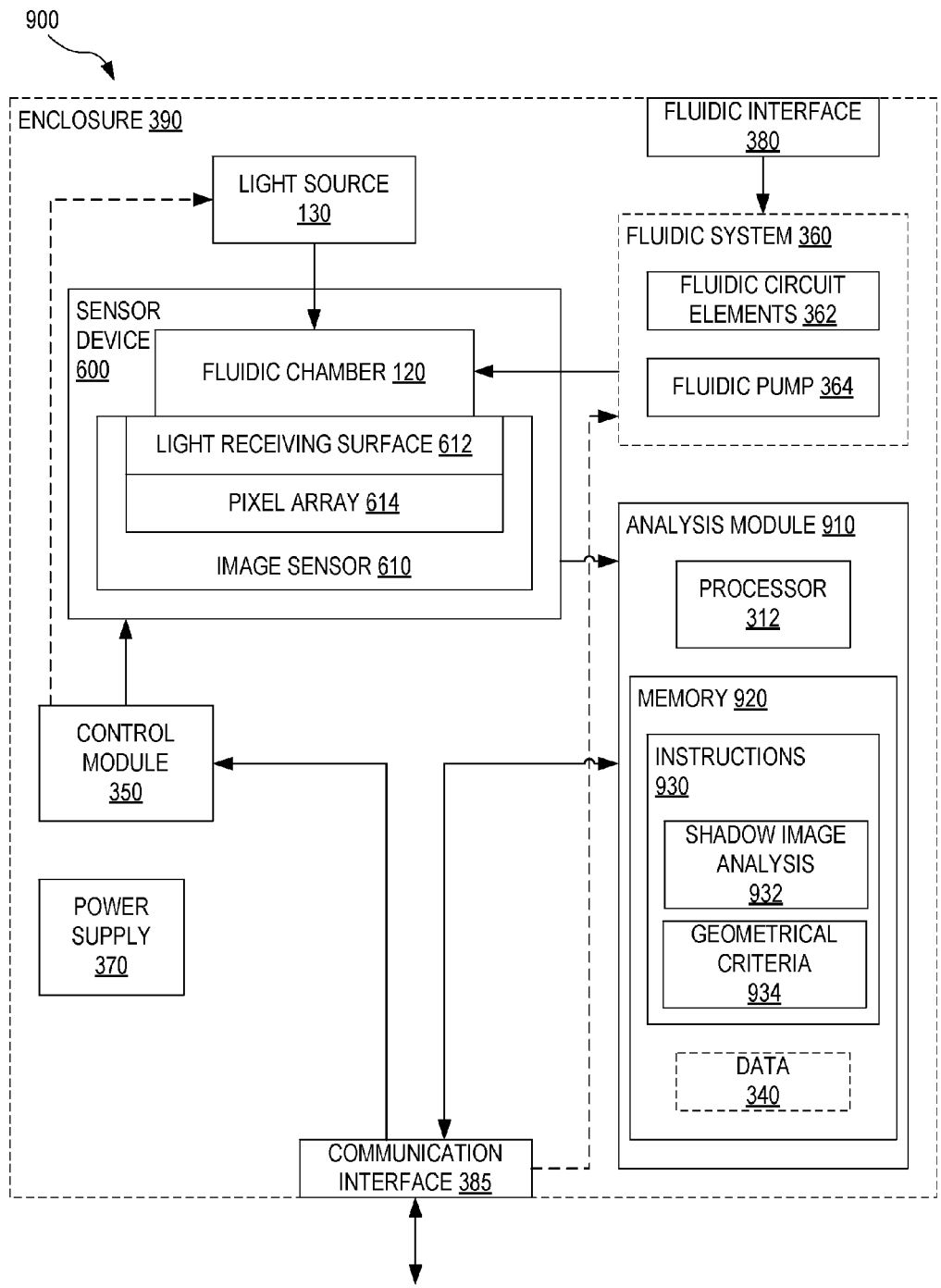
FIG. 9 illustrates one lens-free imaging system for detecting particles in a sample deposited on an image sensor, which includes the sensor device of FIG. 6, according to an embodiment.

FIG. 9 illustrates one exemplary lens-free imaging system 900 for detecting particles, which utilizes lens-free shadow imaging of a sample deposited on the image sensor used to capture the shadow image(s). Lens-free imaging system 900 is an embodiment of lens-free imaging system 100 (FIG. 1) similar to lens-free imaging system 300 (FIG. 3). As compared to lens-free imaging system 300, lens-free imaging system 900 includes sensor device 600 (FIG. 6) instead of sensor device 150 (FIGS. 1, 2, and 3), and includes analysis module 910 instead of analysis module 310 (FIG. 3). Analysis module 910 includes processor 312 (FIG. 3) and memory 920. Memory 920 includes optional data storage 340 (FIG. 3) and machine-readable instructions 930 encoded in a non-volatile portion of memory 920. Instructions 930 include shadow image analysis instructions 932 that, when executed by processor 312, identify particles of interest in shadow images generated by sensor device 600. Instructions 930 further include geometrical criteria 934. Processor 312 retrieves geometrical criteria 934 to identify particles of interest based upon geometrical properties of shadows in shadow images generated by sensor device 600.

Figure 10:
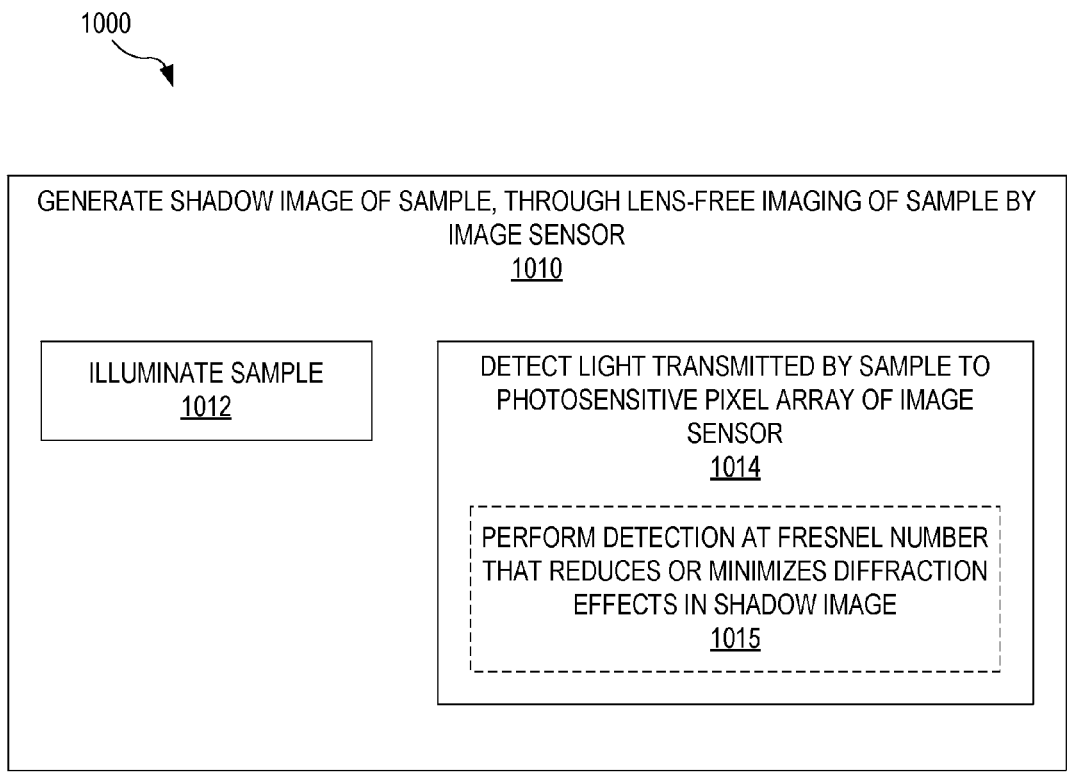
FIG. 10 illustrates one lens-free method for detecting particles in a sample deposited on an image sensor, to generate a shadow image using the image sensor, according to an embodiment.

FIG. 10 illustrates one exemplary method 1000 for generating a shadow image of a sample, deposited on an image sensor, through lens-free imaging of the sample using the image sensor. Method 1000 is an embodiment of step 420 of method 400 (FIG. 4) and may be performed by lens-free imaging system 900 (FIG. 9).

In a step 1010, an image sensor performs lens-free imaging to generate a shadow image of a sample located on the light receiving surface of the image sensor. Step 1010 includes concurrent steps 1012 and 1014. In step 1012, the sample is illuminated. For example, light source 130 (FIGS. 1 and 9) provides illumination 640 (FIG. 6) to illuminated a sample, such as sample 160 (FIG. 1), located in fluidic chamber 120 (FIGS. 1 and 9) of sensor device 600 (FIGS. 6 and 9). In step 1014, light transmitted by the sample is detected using a photosensitive pixel array of the image sensor. For example, pixel array 614 (FIG. 6) detects a portion of illumination light 640 that is transmitted by the sample. In an embodiment, step 1014 includes a step 1015 of performing the detection at a Fresnel number that minimizes or reduces diffraction effects in the shadow image, as discussed in connection with FIGS. 6, 7, and 8.

Figure 11:
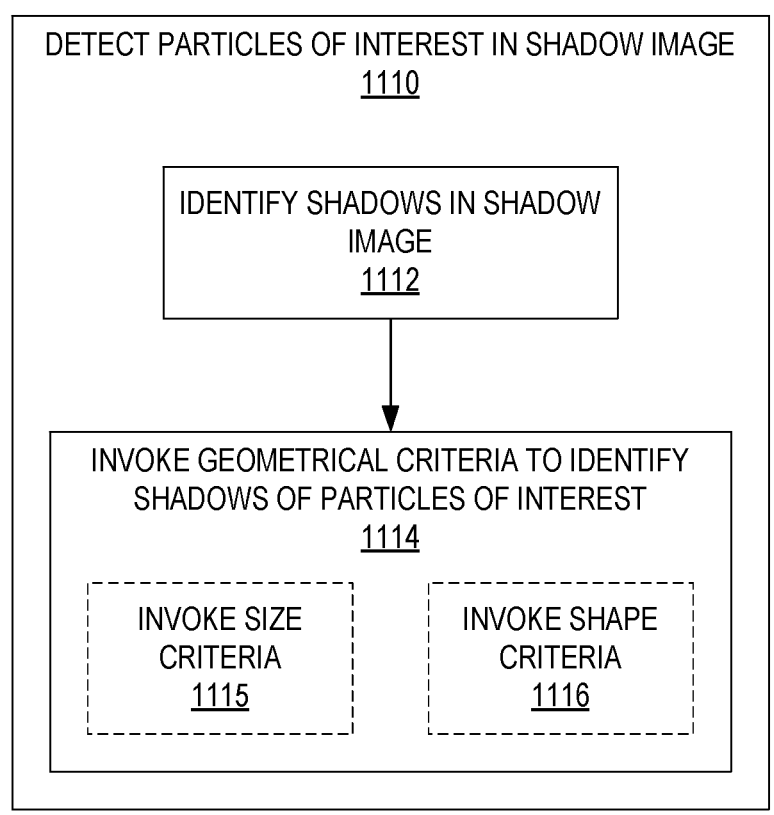
FIG. 11 illustrates one lens-free method for detecting particles in a sample deposited on an image sensor in a shadow image, according to an embodiment.

FIG. 11 illustrates one exemplary method 1100 for detecting particles of interest in a shadow image, such as the shadow image generated by method 1000. Method 1100 is an embodiment of step 430 (FIG. 4). Method 1100 may be performed by lens-free imaging system 900 (FIG. 9).

In a step 1110, particles of interest are detected in the shadow image. Step 1110 includes steps 1112 and 1114. In step 1112, shadows are identified in the shadow image. For example, processor 312 (FIGS. 3 and 9) executes shadow image analysis instructions 932 to identify shadows in a shadow image received from image sensor 610 (FIGS. 6 and 9). For this purpose, shadow image analysis instructions 932 may include methods known in the art, such as thresholding methods and blob-finding methods. In step 1114, geometrical criteria are invoked to identify shadows associated with particles of interest. For example, processor 312 utilizes geometrical criteria 934 (FIG. 9) to identify shadows associated with particles of interest. Step 1114 may include one or both of steps 1115 and 1116 of invoking size criteria and shape criteria, respectively. For example, processor 312 retrieves size criteria and/or shape criteria from geometrical criteria 934 to identify shadows associated with particles of interest.

Figure 12:
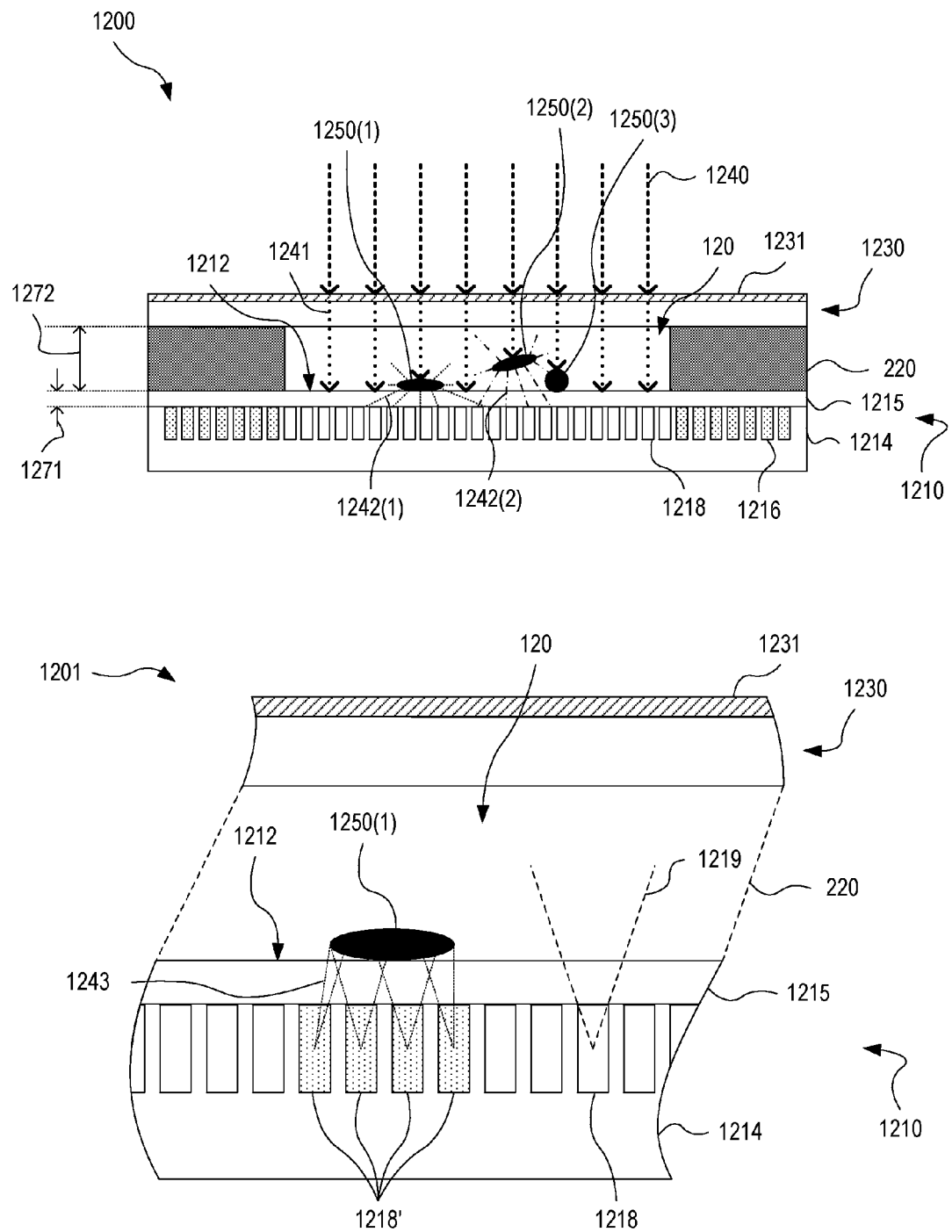
FIG. 12 illustrates one sensor device for lens-free fluorescence imaging of particles in a sample deposited on the image sensor used to image the sample, according to an embodiment.

FIG. 12 illustrates one exemplary sensor device 1200 configured for lens-free fluorescence imaging of a sample deposited on the image sensor used to image the sample. Sensor device 1200 is an embodiment of sensor device 150 (FIGS. 1, 2A, and 2B) tailored for fluorescence imaging. Sensor device 1200 includes an image sensor 1210 and fluidic chamber 120 (FIGS. 1, 2A, and 2B) disposed thereupon. Image sensor 1210 is an embodiment of image sensor 110 (FIGS. 1, 2A, and 2B). FIG. 12 depicts sensor device 1200 in the same cross-sectional view as used in FIG. 2B for sensor device 150.

Image sensor 1210 includes a light receiving surface 1212 and a photosensitive pixel array 1214. Light receiving surface 1212 is, for example, the surface of pixel array 1214 or, as illustrated in FIG. 12, provided by a layer 1215 disposed on pixel array 1214. Light receiving surface 1212, pixel array 1214, and layer 1215 are embodiments of light receiving surface 112, pixel array 114, and layer 210, respectively, of FIG. 2B. Pixel array 1214 is, for example, pixel array 614 of FIG. 6.

Fluidic chamber 120 is formed by light receiving surface 1212 together with walls 220 (FIG. 2B) and a cover 1230 (FIG. 2B), similar to the case of sensor device 150 as discussed in connection with FIGS. 2A and 2B. Pixel array 1214 includes pixels 1218, located underneath fluidic chamber 120, that image a sample therein, and pixels 1216 located underneath walls 220. Pixels 1216 may be dark pixels. Pixels 1218 and 1216 are embodiments of pixels 218 and 216, respectively, of FIG. 2B. For clarity of illustration, not all pixels 1218 and 1216 are labeled in FIG. 12.

Cover 1230 includes a wavelength filter 1231 that filters illumination 1240, for example generated by light source 130 (FIG. 1), to form fluorescence excitation illumination 1241. Wavelength filter 1231 may be included in the light source used to illuminate sensor device 1200, such as light source 130, or be located between sensor device 1200 and the light source, without departing from the scope hereof. Layer 1215 is, or includes, a wavelength filter for at transmitting at least a portion of fluorescence emission generated within fluidic chamber 120 in response to fluorescence excitation illumination 1241. Wavelength filter 1231 is for example a shortpass filter or a bandpass filter. The wavelength filter of layer 1215 is for example a longpass filter or a bandpass filter, which in either case at least partially blocks light below a certain wavelength. In an embodiment, the transmission ranges of wavelength filter 1231 and the wavelength filter of layer 1215 are mutually exclusive, such that none or only a very small portion of fluorescence excitation illumination 1241 is capable of reaching pixel array 1214. In an embodiment, the transmission ranges of wavelength filter 1231 and the wavelength filter of layer 1215, defined at normal incidence of light, are mutually exclusive and further separated by a finite wavelength range to account for non-normal angles of incidence onto one or both of wavelength filter 1231 and the wavelength filter of layer 1215. In an embodiment, illumination 1240 is substantially collimated. In an example, illumination 1240 includes light of a range of wavelengths in the visible spectrum, wavelength filter 1231 blocks at least the majority of the portion of illumination 1240 having wavelength above 500 nanometers, and layer 1215 blocks at least the majority of the portion of light incident thereon and having wavelength less than 500 nanometers.

Image sensor 1210 is configured to capture a fluorescence image of a sample in fluidic chamber 120. The fluorescence image is formed by exposing fluidic chamber 120 to fluorescence excitation illumination 1241. In the exemplary scenario illustrated in FIG. 12, illumination 1240 excites fluorophores on, and/or in, fluorescently labeled particles of interest 1250(1) and 1250(2). Fluorescently labeled particles 1250(1) and 1250(2) respond to fluorescence excitation illumination by emitting fluorescence emission 1242(1) and 1242(2), respectively. Particle 1250(3) is a particle that is not fluorescently labeled. Therefore, particle 1250(3) does not generate fluorescence emission when illuminated with fluorescence excitation illumination 1241. At least portions of fluorescence emission 1242(1) and 1242(2) are transmitted by layer 1215 to pixel array 1214. Hence, pixel array 1214 detects at least portions of fluorescence emission 1242(1) and 1242(2), whereby pixel array 1214 detects fluorescently labeled particles 1250(1) and 1250(2). Since particle 1250 is not fluorescently labeled, particle 1250 is not detected by pixel array 1214. Accordingly, image sensor 1210 generates a fluorescence image of fluorescently labeled particles in a sample deposited in fluidic chamber 120.

FIG. 12 further illustrates a subsection 1201 of sensor device 1200, which includes fluorescently labeled particle 1250(1). Each of pixels 1218 has an acceptance angle 1219. For clarity of illustration, acceptance angle 1219 is indicated only for one pixel 1218. In an embodiment, acceptance angle 1219 and the distance 1271 from light receiving surface 1212 to pixel array 1214 are such that only pixels 1218 located close to fluorescently labeled particle 1250(1) are capable of detecting fluorescence emission originating from fluorescently labeled particle 1250(1). These pixels are labeled 1218'. For pixels 1218', lines 1243 outline the portion of acceptance angle 1219 that includes a line of sight to fluorescently labeled particle 1250(1). Other pixels 1218 do not include a line of sight to fluorescently labeled particle 1250(1) that is within acceptance angle 1219.

In an embodiment, acceptance angle 1219 and distance 1271 are such that only pixels 1218 at locations less than one pixel 1218 away, in a direction parallel to light receiving surface 1212, are capable of detecting fluorescence emission from a fluorescently labeled particle located on light receiving surface 1212. In this embodiment, image sensor 1210 generates a minimally blurred fluorescence image of fluorescently labeled particles on light receiving surface 1212. In another embodiment, acceptance angle 1219 and distance 1271 cooperate to result in the rate of occurrence of overlapping fluorescence events, in an image captured by image sensor 1210 of a sample containing fluorescently labeled particles of interest at a typical concentration, being below a desired threshold. For example, the threshold is set such that fluorescently labeled human blood cells are countable at an accuracy that complies with clinical requirements. In yet another embodiment, acceptance angle 1219 is sufficiently small that an image captured by image sensor 1210 of a sample containing uniformly spaced fluorescently labeled particles of interest at a typical concentration is free of overlapping fluorescence events.

For imaging of samples, in which the particles of interest do not necessarily settle to light receiving surface 1212, blur is minimized when the height 1272 of fluidic chamber 120 is small. Therefore, in certain embodiments of sensor device 1200, height 1272 is the minimal height that allows for depositing the particles of interest in fluidic chamber 120.

In an embodiment, the size of pixels 1218 is significantly smaller than the size of fluorescently labeled particles of interest in fluidic chamber 120, wherein the size of a pixel 1218 is defined as the largest dimension of pixel 1218 in a plane parallel to light receiving surface 1212. This allows for accurate size determination of fluorescently labeled particles of interest, and may further allow for identification of fluorescently labeled particles of interest based upon fluorescence detection and the size of the fluorescence event in the fluorescence image generated by image sensor 1210. For example, fluorescently labeled particles of interest may be found as a subset of detected fluorescence events that further meet specified size criteria. Other geometrical criteria such as shape may be utilized as well for identification of fluorescently labeled particles of interest.

Figure 13:
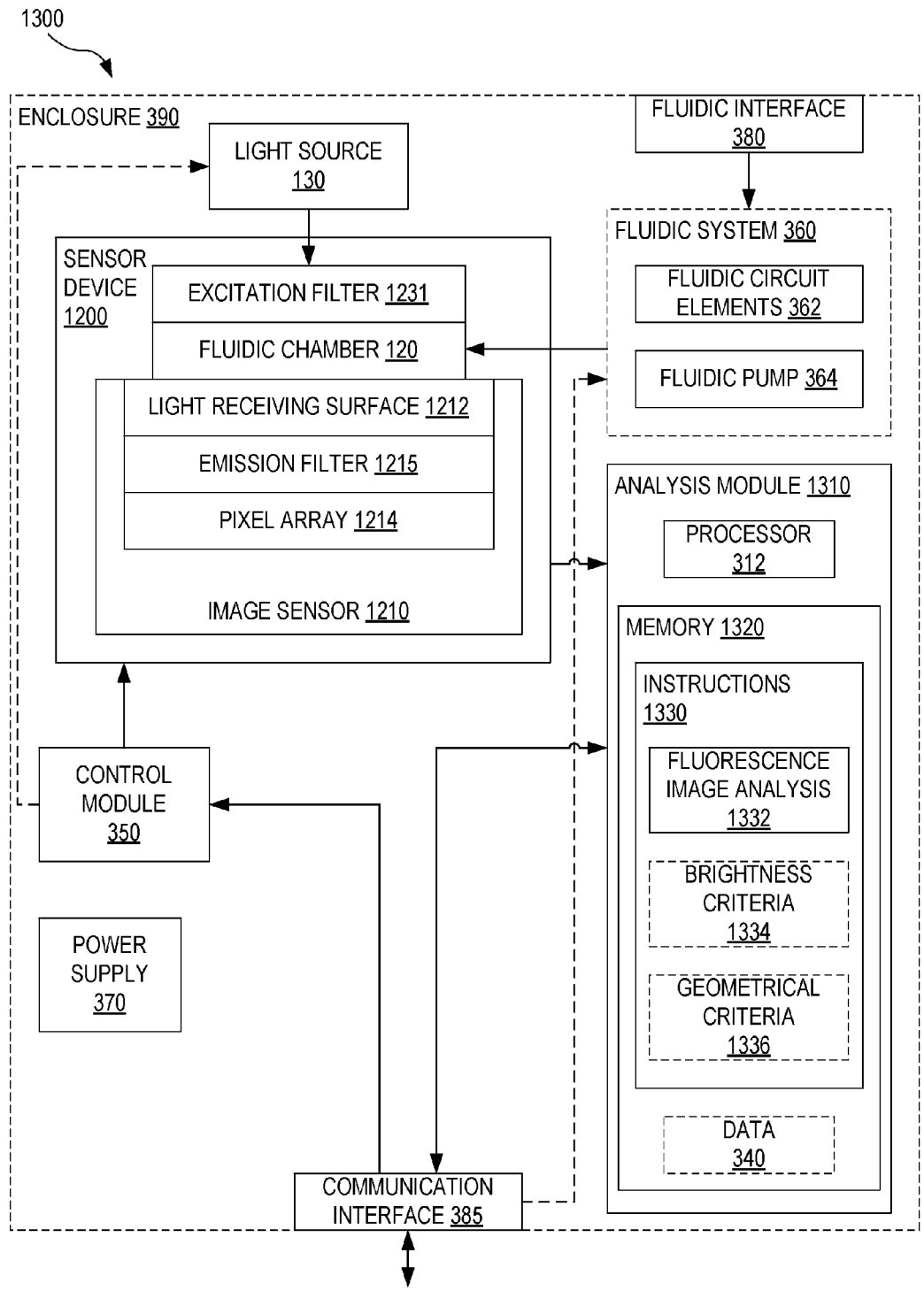
FIG. 13 illustrates one lens-free imaging system for detecting particles in a sample deposited on an image sensor, which includes the sensor device of FIG. 12, according to an embodiment.

FIG. 13 illustrates one exemplary lens-free imaging system 1300 for detecting particles, which utilizes lens-free fluorescence imaging of a sample deposited on the image sensor used to capture the fluorescence image(s). Lens-free imaging system 1300 is an embodiment of lens-free imaging system 100 (FIG. 1) similar to lens-free imaging system 300 (FIG. 3). As compared to lens-free imaging system 300, lens-free imaging system 1300 includes sensor device 1200 (FIG. 12) instead of sensor device 150 (FIGS. 1, 2, and 3), and includes analysis module 1310 instead of analysis module 310 (FIG. 3). Analysis module 1310 includes processor 312 (FIG. 3) and memory 1320. Memory 1320 includes optional data storage 340 (FIG. 3) and machine-readable instructions 1330 encoded in a non-volatile portion of memory 1320. Instructions 1330 include fluorescence image analysis instructions 1332 that, when executed by processor 312, identify particles of interest in shadow images generated by sensor device 1200. In an embodiment, instructions 1330 further include one or both of brightness criteria 1334 and geometrical criteria 1336. Processor 312 retrieves brightness criteria and/or geometrical criteria 1336 to identify particles of interest based upon brightness and geometrical properties, respectively, from fluorescence events in fluorescence images generated by sensor device 1200.

Figure 14:
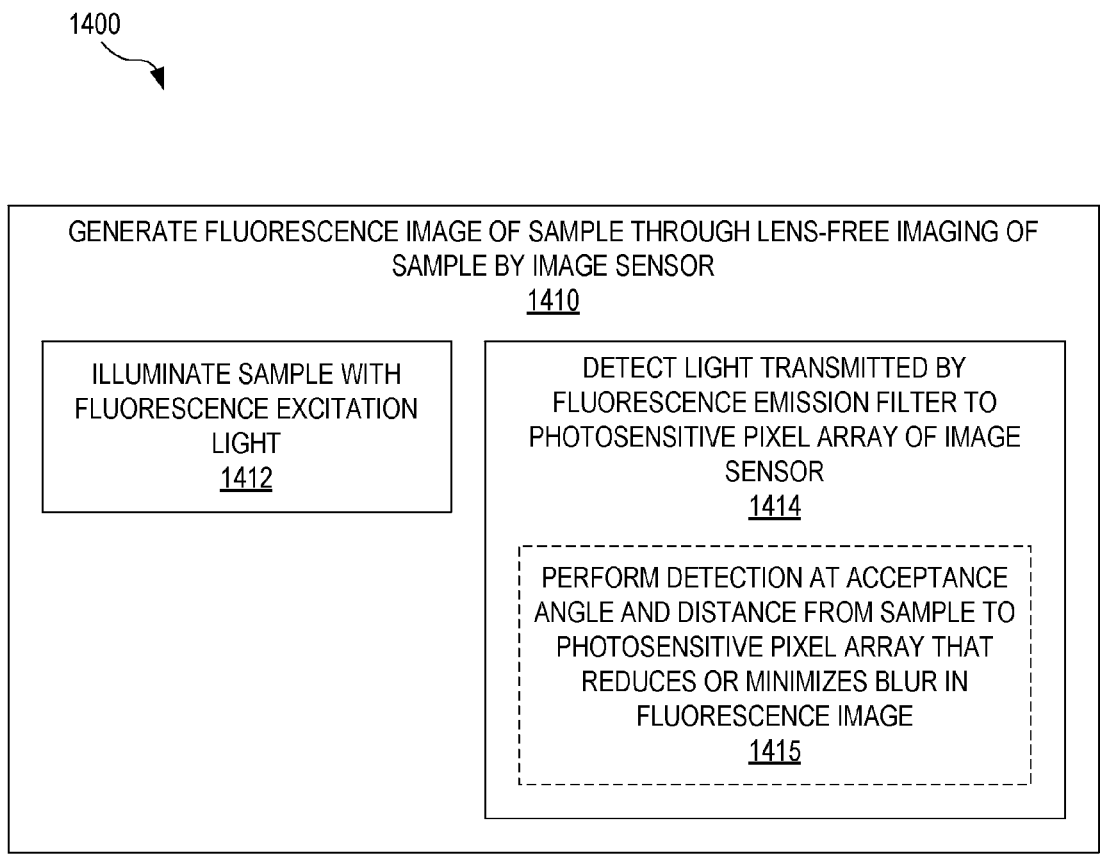
FIG. 14 illustrates one lens-free method for performing lens-free fluorescence imaging, using an image sensor, of particles in a sample deposited on the image sensor, according to an embodiment.

FIG. 14 illustrates one exemplary method 1400 for lens-free fluorescence imaging, using an image sensor, of a sample deposited on the image sensor. Method 1400 is an embodiment of step 420 of method 400 (FIG. 4) and may be performed by lens-free imaging system 1300 (FIG. 13).

In a step 1410, an image sensor performs lens-free imaging to generate a fluorescence image of a sample located on the light receiving surface of the image sensor. Step 1410 includes steps 1412 and 1414. In step 1412, the sample is illuminated with fluorescence excitation light. For example, light source 130 (FIGS. 1 and 13) generates illumination 1240 (FIG. 12) which is filtered by wavelength filter 1231 (FIG. 12) to provide fluorescence excitation illumination 1241 (FIG. 12) to a sample, such as sample 160 (FIG. 1), located in fluidic chamber 120 (FIGS. 1 and 13) of sensor device 1200 (FIGS. 12 and 13). Sample 160 is, for example, a human blood sample with one or more types of blood cells specifically labeled with fluorescent labels. In step 1414, light transmitted by a fluorescence emission filter is detected using a photosensitive pixel array of the image sensor. This transmitted light is, or includes, fluorescence emission. For example, pixel array 1214 (FIG. 12) detects a portion of fluorescence emission 1242(1) and 1242(2) that is transmitted by the wavelength filter of layer 1215 (FIG. 12). In an embodiment, step 1414 includes a step 1415 of performing the detection at an acceptance angle and distance from the sample to the photosensitive pixel array that reduces or minimizes blue in the fluorescence image, as discussed in connection with FIG. 12.

In one embodiment, steps 1412 and 1414 are performed concurrently. In another embodiment, step 1414 is performed after step 1412. This embodiment is relevant for fluorescence imaging of particles labeled with long-lived fluorophores, and may provide improved a signal-to-background ratio since fluorescence images are captured when the sample is not exposed to fluorescence excitation light.

Figure 15:
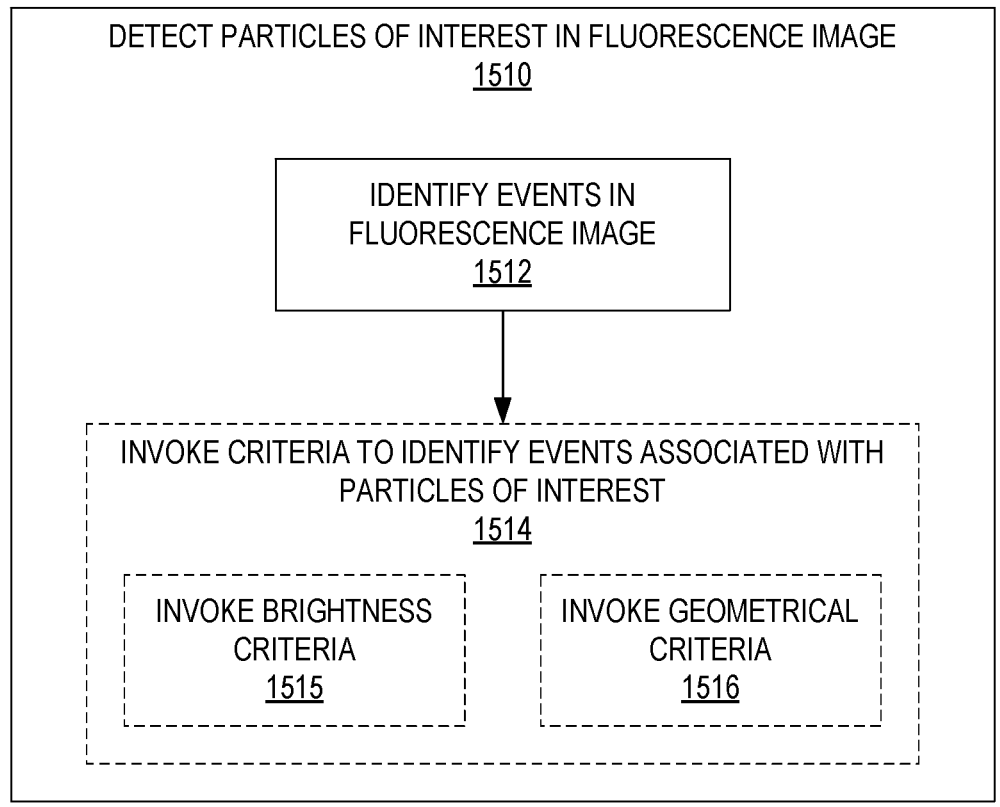
FIG. 15 illustrates one lens-free method for detecting particles in a fluorescence image, according to an embodiment.

FIG. 15 illustrates one exemplary method 1500 for detecting particles of interest in a fluorescence image, such as the fluorescence image generated in method 1400. Method 1500 is an embodiment of step 430 (FIG. 4). Method 1500 is performed, for example, by lens-free imaging system 1300 (FIG. 13).

In a step 1510, particles of interest are detected in the fluorescence image. Step 1510 includes a step 1512 and, optionally, a step 1514. In step 1512, fluorescence events are identified in the fluorescence image. For example, processor 312 (FIGS. 3 and 13) executes fluorescence image analysis instructions 1332 to identify fluorescence events in a fluorescence image received from image sensor 1210 (FIGS. 12 and 13). For this purpose, fluorescence image analysis instructions 1332 may include methods known in the art, such as thresholding methods and blob-finding methods. In optional step 1514, criteria are invoked to identify fluorescence events associated with particles of interest. For example, processor 312 performs one or both of steps 1515 and 1516 to identify fluorescence events associated with particles of interest. In step 1515, brightness criteria 1515 are invoked to identify fluorescence events of brightness consistent with specified brightness criteria. For example processor 312 utilizes brightness criteria 1334 (FIG. 13) to identify fluorescence events associated with particles of interest and, potentially, reject fluorescence events not associated with particles of interest. In step 1516, geometrical criteria are invoked to identify fluorescence events with geometrical properties, such as size and/or shape, associated with particles of interest. For example, processor 312 utilizes geometrical criteria 1336 (FIG. 13) to identify fluorescence events having size and/or shape consistent with particles of interest and, potentially, reject fluorescence events not associated with particles of interest.

Combinations of Features

Features described above as well as those claimed below may be combined in various ways without departing from the scope hereof. For example, it will be appreciated that aspects of one lens-free imaging system, device, or method described herein may incorporate or swap features of another lens-free imaging system, device, or method described herein. The following examples illustrate possible, non-limiting combinations of embodiments described above. It should be clear that many other changes and modifications may be made to the systems, devices, and methods herein without departing from the spirit and scope of this invention:

(A1) A lens-free imaging system for detecting particles in a sample deposited on image sensor may include a fluidic chamber for holding a sample and an image sensor for imaging the sample, wherein the image sensor has a light receiving surface and a plurality of photosensitive pixels disposed underneath the light receiving surface, wherein the fluidic chamber formed at least in part by the light receiving surface.

(A2) The lens-free imaging system denoted as (A1) may further include a light source for illuminating the sample to form an image of the sample on at least a portion of the plurality of photosensitive pixels.

(A3) In the lens-free imaging systems denoted as (A1) and (A2), the image sensor may be a complementary metal-oxide-semiconductor (CMOS) image sensor.

(A4) In the lens-free imaging system denoted as (A3), the image sensor may be a backside illuminated CMOS image sensor.

(A5) In the lens-free imaging systems denoted as (A1) through (A5), the light receiving surface may be at least partially transmissive to light emitted by the light source, and the image may be a shadow image including shadows formed by particles in the sample that block at least a portion of the light emitted by the light source.

(A6) In the lens-free imaging systems denoted as (A1) through (A5), the distance between the light receiving surface and the plurality of photosensitive pixels may be less than one micron.

(A7) In the lens-free imaging systems denoted as (A5) and (A6), the distance from the light receiving surface to the plurality of photosensitive pixels, the size of particles of interest, and the wavelength of light emitted by the light source may be such that the location of maximum intensity of light, from the light source, diffracted by a particle of interest, in the sample and located on the light receiving surface, is less than one photosensitive pixel away from the particle of interest in a direction parallel with the light receiving surface.

(A8) In the lens-free imaging systems denoted as (A5) through (A7), the particle of interest may be a human blood cell, and the distance from the light receiving surface to the plurality of photosensitive pixels, the size of particles of interest, and the wavelength of light emitted by the light source may be such that the location of maximum intensity of light, from the light source, diffracted by a particle of interest, in the sample and located on the light receiving surface, is less than one micron away from the particle of interest in a direction parallel with the light receiving surface.

(A9) In the lens-free imaging systems denoted as (A5) through (A8), the distance from the light receiving surface to the plurality of photosensitive pixels, the size of particles of interest, and the wavelength of light emitted by the light source may form a Fresnel number greater than 75.

(A10) In the lens-free imaging systems denoted as (A5) through (A9), the distance from the light receiving surface to the plurality of photosensitive pixels, the size of particles of interest, and the wavelength of light emitted by the light source may be such that particles of interest in the sample are identifiable using size-selection criteria.

(A11) The lens-free imaging systems denoted as (A1) through (A10) may further include (i) a processor and (ii) instructions, including at least one of size selection criteria and shape selection criteria, that upon execution by the processor identifies particles of interest using the at least one of size criteria and shape criteria.

(A12) In the lens-free imaging systems denoted as (A1) through (A4), the image may be a fluorescence image of fluorescently labeled particles in the sample.

(A13) The lens-free imaging system denoted as (A12) may further include a wavelength filter for transmitting, to the sample, fluorescence excitation illumination and at least partially blocking light of wavelength different from wavelength of the fluorescence excitation illumination.

(A14) In the lens-free imaging systems denoted as (A12) and (A13), the light receiving surface may include a wavelength filter for transmitting fluorescence emission and at least partially blocking the fluorescence excitation illumination.

(A15) The lens-free imaging systems denoted as (A12) through (A14) may further include (i) a processor and (ii) instructions, including a fluorescence brightness criteria, that upon execution by the processor identifies particles of interest using the fluorescence brightness criteria.

(A16) In the lens-free imaging systems denoted as (A1) through (A15), the fluidic chamber may be located over a portion of the plurality of photosensitive pixels, and another portion of the plurality of photosensitive pixels, not located underneath the fluidic chamber, being dark pixels.

(A17) In the lens-free imaging systems denoted as (A1) through (A17), the particles of interest may include human blood cells, or one or more types of human blood cells.

(B1) A method for detecting particles of interest in a sample deposited on an image sensor, through lens-free imaging using the image sensor, may include generating an image of the sample, deposited on a light receiving surface of the image sensor, by illuminating the sample.

(B2) The method denoted as (B1) may further include detecting the particles of interest in the image.

(B3) In the methods denoted as (B1) and (B2), the step of generating an image may further include detecting light using photosensitive pixels of the image sensor, wherein the light passing through only planar surfaces during propagation from the sample to the photosensitive pixels.

(B4) In the methods denoted as (B1) through (B3), the step of generating the image may include generating the image while the sample is flowing across at least a portion of the light receiving surface.

(B5) In the methods denoted as (B1) through (B4), the step of generating the image may include illuminating the image sensor through the sample to form a shadow image of the sample on the image sensor.

(B6) The method denoted as (B5) may include detecting the particles of interest by invoking at least one of size criteria and shape criteria.

(B7) In the methods denoted as (B5) and (B6), the step of generating the image may include generating the image of the sample, wherein the sample is deposited at a distance, measured orthogonal to the light receiving surface, from photosensitive pixels of the image sensor, such that the location of maximum intensity of light associated with the step of illuminating and diffracted by any individual one of the particles of interest is less than one photosensitive pixel away, in dimensions parallel to the light receiving surface, from the individual one of the particles of interest.

(B8) In the methods denoted as (B5) through (B7), the step of generating the image may include generating the image of the sample, wherein the sample is deposited at a distance, measured orthogonal to the light receiving surface, from photosensitive pixels of the image sensor, such that location of maximum intensity of light associated with the step of illuminating and diffracted by any individual one of the particles of interest is less than two micron away, in dimensions parallel to the light receiving surface, from the individual one of the particles of interest.

(B9) The method denoted as (B8) may include detecting particles of interest in the image, which include human blood cells or a type of human blood cell.

(B10) In the methods denoted as (B1) through (B4), the step of generating may include (i) exposing the sample to fluorescence excitation light, and (ii) transmitting, at least partially, fluorescence emission from the sample to photosensitive pixels of the image sensor to form a fluorescence image of fluorescently labeled particles of the sample on the image sensor.

(B11) In the method denoted as (B10), the step of exposing may include wavelength filtering light propagating from the light source towards the sample to generate the fluorescence excitation light.

(B12) In the methods denoted as (B10) and (B11), the step of transmitting fluorescence emission may include wavelength filtering light propagating from the sample to photosensitive pixels to at least partially transmit the fluorescence emission and at least partially block the fluorescence excitation light.

(B13) The methods denoted as (B10) through (B12) may further include detecting the particles of interest by identifying fluorescently labeled particles in the fluorescence image.

(B14) In the methods denoted as (B1) through (B13), the particles of interest may include human blood cells, or one or more types of human blood cells.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present method and device, which, as a matter of language, might be said to fall therebetween.

What is claimed is:

1. A lens-free imaging system for detecting particles in a sample deposited on image sensor, comprising:
    a fluidic chamber for holding a sample and an image sensor for imaging the sample, the image sensor having a light receiving surface and a plurality of photosensitive pixels disposed underneath the light receiving surface, the fluidic chamber formed at least in part by the light receiving surface; and
    a light source for illuminating the sample to form a shadow image of the sample on at least a portion of the plurality of photosensitive pixels, the light receiving surface being at least partially transmissive to light emitted by the light source, the shadow image including shadows formed by particles in the sample that block at least a portion of the light, distance from the light receiving surface to the plurality of photosensitive pixels, size of particles of interest, and wavelength of the light being such that particles of interest in the sample are identifiable in the shadow image using size-selection criteria.

2. The lens-free imaging system of claim 1, the image sensor being a complementary metal-oxide-semiconductor (CMOS) image sensor.

3. The lens-free imaging system of claim 2, the image sensor being a backside illuminated CMOS image sensor.

4. The lens-free imaging system of claim 1, wherein distance between the light receiving surface and the plurality of photosensitive pixels is less than one micron.

5. The lens-free imaging system of claim 1, distance from the light receiving surface to the plurality of photosensitive pixels, size of the particles of interest, and wavelength of the light being such that location of maximum intensity of light diffracted by a particle of interest, in the sample and located on the light receiving surface, is less than one photosensitive pixel away from the particle of interest in a direction parallel with the light receiving surface.

6. The lens-free imaging system of claim 1,
    each particle of interest being a human blood cell; and
    distance from the light receiving surface to the plurality of photosensitive pixels, size of the particles of interest, and wavelength of the light being such that location of maximum intensity of the light diffracted by a particle of interest, in the sample and located on the light receiving surface, is less than one micron away from the particle of interest in a direction parallel with the light receiving surface.

7. The lens-free imaging system of claim 1, distance from the light receiving surface to the plurality of photosensitive pixels, size of particles of interest, and wavelength of light emitted by the light source forming a Fresnel number greater than 75.

8. The lens-free imaging system of claim 1, further comprising:
processor; and
instructions, including size selection criteria, that upon execution by the processor identifies the particles of interest using the size criteria.

9. A lens-free imaging system for detecting particles in a sample deposited on image sensor, comprising:
a fluidic chamber for holding a sample and an image sensor for forming a fluorescence image of the sample, the image sensor having a light receiving surface and a plurality of photosensitive pixels disposed underneath the light receiving surface, the fluidic chamber formed at least in part by the light receiving surface;
a wavelength filter for transmitting, to the sample, fluorescence excitation illumination and at least partially blocking light of wavelength different from wavelength of the fluorescence excitation illumination, the light receiving surface comprising a wavelength filter for transmitting fluorescence emission and at least partially blocking the fluorescence excitation illumination.

10. The lens-free imaging system of claim 9, further comprising:
a processor; and
instructions, including a fluorescence brightness criteria, that upon execution by the processor identifies particles of interest using the fluorescence brightness criteria.

11. The lens-free imaging system of claim 1, the fluidic chamber being located over a portion of the plurality of photosensitive pixels, and another portion of the plurality of photosensitive pixels, not located underneath the fluidic chamber, being dark pixels.

12. A method for detecting particles of interest in a sample deposited on an image sensor, through lens-free imaging using the image sensor, comprising:
generating an image of the sample, deposited on a light receiving surface of the image sensor, by illuminating the image sensor through the sample to form a shadow image of the sample on the image sensor, the sample being deposited at a distance, measured orthogonal to the light receiving surface, from photosensitive pixels of the image sensor, such that location of maximum intensity of light associated with said illuminating and diffracted by any individual one of the particles of interest is less than one photosensitive pixel away, in dimensions parallel to the light receiving surface, from the individual one of the particles of interest; and
detecting the particles of interest in the image.

13. The method of claim 12, the step of generating an image further comprising detecting light using photosensitive pixels of the image sensor, the light passing through only planar surfaces during propagation from the sample to the photosensitive pixels.

14. The method of claim 12, the step of generating the image comprising generating the image while the sample is flowing across at least a portion of the light receiving surface.

15. The method of claim 12, the step of detecting the particles of interest comprising invoking at least one of size criteria and shape criteria.

16. The method of claim 12,
the step of detecting the particles of interest comprising identifying human blood cells in the image.

17. A method for detecting particles of interest in a sample deposited on an image sensor, through lens-free imaging using the image sensor, comprising:
generating a fluorescence image of fluorescently labeled particles of the sample, deposited on a light receiving surface of the image sensor, by
(a) exposing the sample to fluorescence excitation light, said exposing including wavelength filtering light propagating from the light source towards the sample to generate the fluorescence excitation light, and
(b) transmitting, at least partially, fluorescence emission from the sample to photosensitive pixels of the image sensor to form the fluorescence image of fluorescently labeled particles of the sample on the image sensor, said transmitting fluorescence emission including wavelength filtering light propagating from the sample to photosensitive pixels of the image sensor to at least partially transmit the fluorescence emission and at least partially block the fluorescence excitation light; and
detecting the particles of interest in the fluorescence image.

18. The method of claim 17, the step of detecting the particles of interest comprising identifying fluorescently labeled particles in the fluorescence image.

19. The lens-free imaging system of claim 9, further comprising a light source for generating the fluorescence excitation illumination.

20. The lens-free imaging system of claim 9, the image sensor being a complementary metal-oxide-semiconductor (CMOS) image sensor.

21. The lens-free imaging system of claim 20, the image sensor being a backside illuminated CMOS image sensor.

22. The lens-free imaging system of claim 9, the fluidic chamber being located over a portion of the plurality of photosensitive pixels, and another portion of the plurality of photosensitive pixels, not located underneath the fluidic chamber, being dark pixels.

23. The method of claim 17, the step of generating the fluorescence image further comprising detecting light using photosensitive pixels of the image sensor, the light passing through only planar surfaces during propagation from the sample to the photosensitive pixels.

24. The method of claim 17, the step of generating the fluorescence comprising generating the fluorescence image while the sample is flowing across at least a portion of the light receiving surface.

25. The method of claim 17, the step of detecting the particles of interest comprising identifying human blood cells in the image.

* * * * *